(12) United States Patent
Poulsen et al.

(10) Patent No.: US 8,293,239 B2
(45) Date of Patent: Oct. 23, 2012

(54) METHODS OF TREATING CHRONIC PAIN

(75) Inventors: Kristian Todd Poulsen, San Francisco, CA (US); David Louis Shelton, Alameda, CA (US); Joerg Zeller, San Francisco, CA (US); Ian Machin, Sandwich (GB); Laura Corradini, Sandwich (GB)

(73) Assignee: Pfizer Limited, Sandwich, Kent (GB)

( * ) Notice: Subject to any disclaimer, the term of this patent is extended or adjusted under 35 U.S.C. 154(b) by 50 days.

(21) Appl. No.: 12/920,621

(22) PCT Filed: Mar. 3, 2009

(86) PCT No.: PCT/IB2009/050852
§ 371 (c)(1),
(2), (4) Date: Sep. 2, 2010

(87) PCT Pub. No.: WO2009/109911
PCT Pub. Date: Sep. 11, 2009

(65) Prior Publication Data
US 2011/0257371 A1    Oct. 20, 2011

Related U.S. Application Data

(60) Provisional application No. 61/033,558, filed on Mar. 4, 2008.

(51) Int. Cl.
*A61K 39/395* (2006.01)
*C12P 21/08* (2006.01)
*C07K 16/00* (2006.01)

(52) U.S. Cl. ............... 424/145.1; 424/130.1; 424/133.1; 424/141.1; 530/387.1; 530/387.3; 530/388.1; 530/388.24

(58) Field of Classification Search ........................ None
See application file for complete search history.

(56) References Cited

U.S. PATENT DOCUMENTS

| | | | | |
|---|---|---|---|---|
| 7,479,488 B2 | 1/2009 | Mueller et al. | ................. | 514/221 |
| 2006/0183700 A1 | 8/2006 | Vater et al. | ....................... | 514/44 |

FOREIGN PATENT DOCUMENTS

| | | |
|---|---|---|
| EP | 1770091 | 4/2007 |
| WO | WO03093472 | 11/2003 |
| WO | WO2007054809 | 5/2007 |
| WO | WO2007061676 | 5/2007 |
| WO | WO2007076336 | 7/2007 |
| WO | WO2008011190 | 1/2008 |

OTHER PUBLICATIONS

Rudikoff et al. (1982). Single amino acid substitution altering antigen-binding specificity. Proc. Natl. Acad. Sci. USA. 79:1979-1983.*
PCT/IB2009/050852 International Search Report dated Jul. 10, 2009.
Kuraishi, et al., "Antinociception induced in rats by intrathecal administration of antiserum against calcitonin gene-related peptide", *Neuroscience Letters*, vol. 92(3), pp. 325-329 (1988).
Kawamura, et al., "Antinociceptive effect of intrathecally administered antiserum against calcitonin gene-related peptide on thermal and mechanical noxious stimuli in experimental hyperalgesic rats", *Brain Research*, vol. 497(1): pp. 199-203 (1989).
Zeller, et al., "CGRP function-blocking antibodies inhibit neurogenic vasodilation without affecting heart rate of arterial blood pressure in the rat", *British Journal of Pharmacology*, vol. 155(7), pp. 1093-1103 (2008).
Bennett, et al., "Alleviation of mechanical and thermal allodynia by CGRP8-37 in a rodent model of chronic central pain", *Pain*, vol. 86(1); pp. 163-175 (2000).
Tzabazis, et al., "Antihyperalgesic effect of a recombinant herpes virus encoding antisense for calcitonin gene-related peptide", *Anesthesiology*, vol. 106(6), pp. 1196-1203 (2007).
Wong, et al., "Monoclonal antibody to rat alpha-CGRP: Production, characterization, and in vivo immunoneutralization activity", *Hybridoma*, vol. 12(1), pp. 93-106 (1993).
Tan, et al., "Calcitonin gene-related peptide as an endogenous vasodilator: immunoblockade studies in vivo with an anti-calcitonin gene-related peptide monoclonal antibody and its FAB' fragment", *Clinical Science*, vol. 89(6), pp. 565-573 (1995).
Adwanikar, et al., "Spinal CGRP1 receptors contribute to supraspinally organized pain behavior and pain-related sensitization of amygdale neurons", *Pain*, vol. 132(1-2), pp. 53-66 (2007).
Plourde, et al, "CGRP antagonists and capsaicin on celiac ganglia partly prevent postoperative gastric ileus", *Peptides*, vol. 14(6); pp. 1225-1229 (1993).
Ambalavanar, et al., "Deep tissue inflammation upregulates neuropeptiteds and evokes nociceptive behaviors which are modulated by neuropeptide antagonist", *Pain*, vol. 120(1-2), pp. 53-68 (2006).
Wick, et al, "Transient receptor potential vanilloid 1, calcitonin gene-related peptide, and substance P mediate nociception in acute pancreatitis", *American Journal of Physiology Gastrointest Liver Physiol.*, vol. 290(5); pp. G959-G969 (2006).

* cited by examiner

*Primary Examiner* — Christine J Saoud
*Assistant Examiner* — Jon M Lockard
(74) *Attorney, Agent, or Firm* — Susan L. Wang

(57) ABSTRACT

The invention relates to an anti-CGRP antibody for use in the prevention and/or treatment of chronic pain and/or symptoms of chronic pain, and to a method of treating and/or preventing chronic pain and/or symptoms of chronic pain using an anti-CGRP antibody.

14 Claims, 10 Drawing Sheets

NH2-*A*C*D*TATCVTHRLA*G*LLSRSGG*V*VK*N*NFVPT*N*VGS_K_AF-CONH2
Human α-CGRP (identical to *cynomolgus* α-CGRP)

NH2-*A*C*N*TATCVTHRLA*G*LLSRSGG*M*VK*S*NFVPT*N*VGS_K_AF-CONH2
Human β-CGRP (identical to *cynomolgus* β-CGRP)

NH2-*S*C*N*TATCVTHRLA*G*LLSRSGG*V*VK*D*NFVPT*N*VGS_E_AF-CONH2
Rat α-CGRP (identical to mouse and dog α-CGRP)

NH2-*S*C*N*TATCVTHRLA*G*LLSRSGG*V*VK*D*NFVPT*N*VGS_K_AF-CONH2
Rat β-CGRP

NH2-*S*C*N*TATCVTHRLA*D*LLSRSGG*V*LK*D*NFVPT*D*VGS_E_AF-CONH2
Mouse β-CGRP

NH2-*G*C*N*TATCVTHRLA*G*LLSRSGG*M*VK*S*NFVPT*N*VGS_E_AF-CONH2
Rabbit CGRP

Figure 8

SEQUENCE LISTING

```
<160> NUMBER OF SEQ ID NOS: 32

<210> SEQ ID NO 1
<211> LENGTH: 122
<212> TYPE: PRT
<213> ORGANISM: Artificial sequence
<220> FEATURE:
<223> OTHER INFORMATION: Synthetic polypeptide, Antibody G1 heavy chain
      variable region

<400> SEQUENCE: 1

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Asn Tyr
            20                  25                  30

Trp Ile Ser Trp Val Arg Gln Ala Pro Gly Lys Gly Leu Glu Trp Val
            35                  40                  45

Ala Glu Ile Arg Ser Glu Ser Asp Ala Ser Ala Thr His Tyr Ala Glu
 50                  55                  60

Ala Val Lys Gly Arg Phe Thr Ile Ser Arg Asp Asn Ala Lys Asn Ser
 65                  70                  75                  80

Leu Tyr Leu Gln Met Asn Ser Leu Arg Ala Glu Asp Thr Ala Val Tyr
            85                  90                  95

Tyr Cys Leu Ala Tyr Phe Asp Tyr Gly Leu Ala Ile Gln Asn Tyr Trp
            100                 105                 110

Gly Gln Gly Thr Leu Val Thr Val Ser Ser
            115                 120

<210> SEQ ID NO 2
<211> LENGTH: 107
<212> TYPE: PRT
<213> ORGANISM: Artificial sequence
<220> FEATURE:
<223> OTHER INFORMATION: Synthetic polypeptide, Antibody G1 light chain
      variable region

<400> SEQUENCE: 2

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Lys Arg Val Thr Thr Tyr
            20                  25                  30

Val Ser Trp Tyr Gln Gln Lys Pro Gly Gln Ala Pro Arg Leu Leu Ile
            35                  40                  45

Tyr Gly Ala Ser Asn Arg Tyr Leu Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Ser Gln Ser Tyr Asn Tyr Pro Tyr
            85                  90                  95

Thr Phe Gly Gln Gly Thr Lys Leu Glu Ile Lys
            100                 105

<210> SEQ ID NO 3
<211> LENGTH: 10
<212> TYPE: PRT
<213> ORGANISM: Artificial sequence
<220> FEATURE:
<223> OTHER INFORMATION: Synthetic polypeptide, Antibody G1 CDR H1

<400> SEQUENCE: 3

Gly Phe Thr Phe Ser Asn Tyr Trp Ile Ser
1               5                   10

<210> SEQ ID NO 4
<211> LENGTH: 19
<212> TYPE: PRT
<213> ORGANISM: Artificial sequence
<220> FEATURE:
<223> OTHER INFORMATION: Synthetic polypeptide, Antibody G1 CDR H2

<400> SEQUENCE: 4

Glu Ile Arg Ser Glu Ser Asp Ala Ser Ala Thr His Tyr Ala Glu Ala
1               5                   10                  15
```

Val Lys Gly

<210> SEQ ID NO 5
<211> LENGTH: 11
<212> TYPE: PRT
<213> ORGANISM: Artificial sequence
<220> FEATURE:
<223> OTHER INFORMATION: Synthetic polypeptide, Antibody G1 CDR H3

<400> SEQUENCE: 5

Tyr Phe Asp Tyr Gly Leu Ala Ile Gln Asn Tyr
1               5                   10

<210> SEQ ID NO 6
<211> LENGTH: 11
<212> TYPE: PRT
<213> ORGANISM: Artificial sequence
<220> FEATURE:
<223> OTHER INFORMATION: Synthetic polypeptide, Antibody G1 CDR L1

<400> SEQUENCE: 6

Lys Ala Ser Lys Arg Val Thr Thr Tyr Val Ser
1               5                   10

<210> SEQ ID NO 7
<211> LENGTH: 7
<212> TYPE: PRT
<213> ORGANISM: Artificial sequence
<220> FEATURE:
<223> OTHER INFORMATION: Synthetic polypeptide, Antibody G1 CDR L2

<400> SEQUENCE: 7

Gly Ala Ser Asn Arg Tyr Leu
1               5

<210> SEQ ID NO 8
<211> LENGTH: 9
<212> TYPE: PRT
<213> ORGANISM: Artificial sequence
<220> FEATURE:
<223> OTHER INFORMATION: Synthetic polypeptide, Antibody G1 CDR L3

<400> SEQUENCE: 8

Ser Gln Ser Tyr Asn Tyr Pro Tyr Thr
1               5

<210> SEQ ID NO 9
<211> LENGTH: 366
<212> TYPE: DNA
<213> ORGANISM: Artificial sequence
<220> FEATURE:
<223> OTHER INFORMATION: Synthetic oligonucleotide, Antibody G1 heavy
      chain variable region

<400> SEQUENCE: 9
gaagttcagc tggttgaatc cggtggtggt ctggttcagc caggtggttc cctgcgtctg      60
tcctgcgctg cttccggttt cacctctcc aactactgga tctcctgggt tcgtcaggct     120
cctggtaaag gtctggaatg ggttgctgaa atccgttccg aatccgacgc gtccgctacc    180
cattacgctg aagctgttaa aggtcgtttc accatctccc gtgacaacgc taagaactcc    240
ctgtacctgc agatgaactc cctgcgtgct gaagacaccg ctgtttacta ctgcctggct    300
tactttgact acggtctggc tatccagaac tactggggtc agggtaccct ggttaccgtt    360
tcctcc                                                              366

<210> SEQ ID NO 10
<211> LENGTH: 321
<212> TYPE: DNA
<213> ORGANISM: Artificial sequence
<220> FEATURE:
<223> OTHER INFORMATION: Synthetic oligonucleotide, Antibody G1 light
      chain variable region

<400> SEQUENCE: 10

```
gaaatcgttc tgacccagtc cccggctacc ctgtccctgt ccccaggtga acgtgctacc      60
ctgtcctgca aagcttccaa cgggttacc acctacgttt cctggtacca gcagaaaccc     120
ggtcaggctc ctcgtctgct gatctacggt gcttccaacc gttacctcgg tatcccagct     180
cgtttctccg gttccggttc cggtaccgac ttcaccctga ccatctcctc cctggaaccc     240
gaagacttcg ctgtttacta ctgcagtcag tcctacaact accccctacac cttcggtcag     300 ggtaccaaac tggaaatcaa a                                                321
```

<210> SEQ ID NO 11
<211> LENGTH: 448
<212> TYPE: PRT
<213> ORGANISM: Artificial sequence
<220> FEATURE:
<223> OTHER INFORMATION: Synthetic polypeptide, Antibody G1 heavy chain

<400> SEQUENCE: 11

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Ile Ser Trp Val Arg Gln Ala Pro Gly Lys Gly Leu Glu Trp Val
        35                  40                  45

Ala Glu Ile Arg Ser Glu Ser Asp Ala Ser Ala Thr His Tyr Ala Glu
    50                  55                  60

Ala Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Leu Ala Tyr Phe Asp Tyr Gly Leu Ala Ile Gln Asn Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255
```

Thr Pro Glu Val Thr Cys Val Val Asp Val Ser His Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Phe Arg Val Val
290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Thr Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 12
<211> LENGTH: 214
<212> TYPE: PRT
<213> ORGANISM: Artificial sequence
<220> FEATURE:
<223> OTHER INFORMATION: Synthetic polypeptide, Antibody G1 light chain

<400> SEQUENCE: 12

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Lys Arg Val Thr Thr Tyr
            20                  25                  30

Val Ser Trp Tyr Gln Gln Lys Pro Gly Gln Ala Pro Arg Leu Leu Ile
        35                  40                  45

Tyr Gly Ala Ser Asn Arg Tyr Leu Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Ser Gln Ser Tyr Asn Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr

Ala Cys Glu Val Thr His Gln Gly Leu Ser Ser Pro Val Thr Lys Ser
        195                 200                 205

Phe Asn Arg Gly Glu Cys
    210

<210> SEQ ID NO 13
<211> LENGTH: 1347
<212> TYPE: DNA
<213> ORGANISM: Artificial sequence
<220> FEATURE:
<223> OTHER INFORMATION: Synthetic oligonucleotide, Antibody G1 heavy
      chain

<400> SEQUENCE: 13

| | | | | | |
|---|---|---|---|---|---|
| gaagttcagc | tggttgaatc | cggtggtggt | ctggttcagc | caggtggttc | cctgcgtctg | 60 |
| tcctgcgctg | cttccggttt | caccttctcc | aactactgga | tctcctgggt | tcgtcaggct | 120 |
| cctggtaaag | gtctggaatg | ggttgctgaa | atccgttccg | aatccgacgc | gtccgctacc | 180 |
| cattacgctg | aagctgttaa | aggtcgtttc | accatctccc | gtgacaacgc | taagaactcc | 240 |
| ctgtacctgc | agatgaactc | cctgcgtgct | gaagacaccg | ctgtttacta | ctgcctggct | 300 |
| tactttgact | acggtctggc | tatccagaac | tactggggtc | agggtaccct | ggttaccgtt | 360 |
| tcctccgcct | ccaccaaggg | cccatctgtc | ttcccactgg | ccccatgctc | cgcagcacc | 420 |
| tccgagagca | cagccgccct | gggctgcctg | gtcaaggact | acttcccaga | acctgtgacc | 480 |
| gtgtcctgga | actctggcgc | tctgaccagc | ggcgtgcaca | ccttcccagc | tgtcctgcag | 540 |
| tcctcaggtc | tctactccct | cagcagcgtg | gtgaccgtgc | catccagcaa | cttcggcacc | 600 |
| cagacctaca | cctgcaacgt | agatcacaag | ccaagcaaca | ccaaggtcga | caagaccgtg | 660 |
| gagagaaagt | gttgtgtgga | gtgtccacct | tgtccagccc | ctcagtggc | cggaccatcc | 720 |
| gtgttcctgt | tcctccaaa | gccaaaggac | accctgatga | tctccagaac | cccagaggtg | 780 |
| acctgtgtgg | tggtggacgt | gtcccacgag | gacccagagg | tgcagttcaa | ctggtatgtg | 840 |
| gacggagtgg | aggtgcacaa | cgccaagacc | aagccaagag | aggagcagtt | caactccacc | 900 |
| ttcagagtgg | tgagcgtgct | gaccgtggtg | caccaggact | ggctgaacgg | aaaggagtat | 960 |
| aagtgtaagg | tgtccaacaa | gggactgcca | tccagcatcg | agaagaccat | ctccaagacc | 1020 |
| aagggacagc | caagagagcc | acaggtgtat | accctgcccc | catccagaga | ggagatgacc | 1080 |
| aagaaccagg | tgtccctgac | ctgtctggtg | aagggattct | atccatccga | catcgccgtg | 1140 |
| gagtgggagt | ccaacggaca | gccagagaac | aactataaga | ccacccctcc | aatgctggac | 1200 |
| tccgacggat | ccttcttcct | gtattccaag | ctgaccgtgg | acaagtccag | atggcagcag | 1260 |
| ggaaacgtgt | tctcttgttc | cgtgatgcac | gaggccctgc | acaaccacta | cccagaaag | 1320 |
| agcctgtccc | tgtctccagg | aaagtaa | | | | 1347 |

<210> SEQ ID NO 14
<211> LENGTH: 645
<212> TYPE: DNA
<213> ORGANISM: Artificial sequence
<220> FEATURE:
<223> OTHER INFORMATION: Synthetic oligonucleotide, Antibody G1 light
      chain

<400> SEQUENCE: 14

| | | | | | |
|---|---|---|---|---|---|
| gaaatcgttc | tgacccagtc | cccggctacc | ctgtccctgt | cccaggtga | acgtgctacc | 60 |
| ctgtcctgca | aagcttccaa | acgggttacc | acctacgttt | cctggtacca | gcagaaaccc | 120 |

```
ggtcaggctc ctcgtctgct gatctacggt gcttccaacc gttacctcgg tatcccagct    180
cgtttctccg gttccggttc cggtaccgac ttcaccctga ccatctcctc cctggaaccc    240
gaagacttcg ctgtttacta ctgcagtcag tcctacaact acccctacac cttcggtcag    300
ggtaccaaac tggaaatcaa acgcactgtg gctgcaccat ctgtcttcat cttccctcca    360
tctgatgagc agttgaaatc cggaactgcc tctgttgtgt gcctgctgaa taacttctat    420
ccgcgcgagg ccaaagtaca gtggaaggtg gataacgccc tccaatccgg taactcccag    480
gagagtgtca cagagcagga cagcaaggac agcacctaca gcctcagcag caccctgacc    540
ctgagcaaag cagactacga gaaacacaaa gtctacgcct gcgaagtcac ccatcagggc    600
ctgagttctc cagtcacaaa gagcttcaac cgcggtgagt gctaa                    645
```

<210> SEQ ID NO 15
<211> LENGTH: 37
<212> TYPE: PRT
<213> ORGANISM: Homo sapiens
<220> FEATURE:
<223> OTHER INFORMATION: Polypeptide, Alpha-CGRP

<400> SEQUENCE: 15

Ala Cys Asp Thr Ala Thr Cys Val Thr His Arg Leu Ala Gly Leu Leu
1               5                   10                  15

Ser Arg Ser Gly Gly Val Val Lys Asn Asn Phe Val Pro Thr Asn Val
            20                  25                  30

Gly Ser Lys Ala Phe
        35

<210> SEQ ID NO 16
<211> LENGTH: 37
<212> TYPE: PRT
<213> ORGANISM: Homo sapiens
<220> FEATURE:
<223> OTHER INFORMATION: Polypeptide, Beta-CGRP

<400> SEQUENCE: 16

Ala Cys Asn Thr Ala Thr Cys Val Thr His Arg Leu Ala Gly Leu Leu
1               5                   10                  15

Ser Arg Ser Gly Gly Met Val Lys Ser Asn Phe Val Pro Thr Asn Val
            20                  25                  30

Gly Ser Lys Ala Phe
        35

<210> SEQ ID NO 17
<211> LENGTH: 37
<212> TYPE: PRT
<213> ORGANISM: Rattus norvegicus
<220> FEATURE:
<223> OTHER INFORMATION: Polypeptide, Alpha-CGRP

<400> SEQUENCE: 17

Ser Cys Asn Thr Ala Thr Cys Val Thr His Arg Leu Ala Gly Leu Leu
1               5                   10                  15

Ser Arg Ser Gly Gly Val Val Lys Asp Asn Phe Val Pro Thr Asn Val
            20                  25                  30

Gly Ser Glu Ala Phe
        35

<210> SEQ ID NO 18
<211> LENGTH: 37
<212> TYPE: PRT
<213> ORGANISM: Rattus norvegicus

```
<220> FEATURE:
<223> OTHER INFORMATION: Polypeptide, Beta-CGRP

<400> SEQUENCE: 18

Ser Cys Asn Thr Ala Thr Cys Val Thr His Arg Leu Ala Gly Leu Leu
1               5                   10                  15

Ser Arg Ser Gly Gly Val Val Lys Asp Asn Phe Val Pro Thr Asn Val
            20                  25                  30

Gly Ser Lys Ala Phe
        35

<210> SEQ ID NO 19
<211> LENGTH: 115
<212> TYPE: PRT
<213> ORGANISM: Artificial sequence
<220> FEATURE:
<223> OTHER INFORMATION: Synthetic polypeptide, Antibody G2 heavy chain
      variable region

<400> SEQUENCE: 19

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Ser
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Lys Gly Gly Asn Asp Gly Tyr Trp Gly Gln Gly Thr Thr Leu Thr
            100                 105                 110

Val Ser Ser
        115

<210> SEQ ID NO 20
<211> LENGTH: 108
<212> TYPE: PRT
<213> ORGANISM: Artificial sequence
<220> FEATURE:
<223> OTHER INFORMATION: Synthetic polypeptide, Antibody G2 light chain
      variable region

<400> SEQUENCE: 20

Glu Ile Val Leu Thr Gln Ser Pro Thr Thr Met Ala Ala Ser Pro Gly
1               5                   10                  15

Glu Lys Ile Thr Ile Thr Cys Ser Ala Ser Ser Ser Ile Ser Ser Ile
            20                  25                  30

Tyr Leu His Trp Tyr Gln Gln Lys Pro Gly Phe Ser Pro Lys Val Leu
        35                  40                  45

Ile Tyr Arg Ala Ser Asn Leu Ala Ser Gly Val Pro Ala Arg Phe Ser
    50                  55                  60

Gly Ser Gly Ser Gly Thr Ser Tyr Ser Leu Thr Ile Gly Thr Met Glu
65                  70                  75                  80

Ala Glu Asp Val Ala Thr Tyr Tyr Cys Gln Gln Gly Ser Thr Ile Pro
                85                  90                  95

Phe Thr Phe Gly Ser Gly Thr Lys Leu Glu Ile Lys
            100                 105
```

```
<210> SEQ ID NO 21
<211> LENGTH: 5
<212> TYPE: PRT
<213> ORGANISM: Artificial sequence
<220> FEATURE:
<223> OTHER INFORMATION: Synthetic polypeptide, Antibody G2 CDR H1

<400> SEQUENCE: 21

Ser Ser Val Met His
1               5

<210> SEQ ID NO 22
<211> LENGTH: 17
<212> TYPE: PRT
<213> ORGANISM: Artificial sequence
<220> FEATURE:
<223> OTHER INFORMATION: Synthetic polypeptide, Antibody G2 CDR H2

<400> SEQUENCE: 22

Tyr Ile Asn Pro Tyr Asn Asp Gly Thr Lys Tyr Asn Glu Lys Phe Lys
1               5                   10                  15

Gly

<210> SEQ ID NO 23
<211> LENGTH: 6
<212> TYPE: PRT
<213> ORGANISM: Artificial sequence
<220> FEATURE:
<223> OTHER INFORMATION: Synthetic polypeptide, Antibody G2 CDR H3

<400> SEQUENCE: 23

Gly Gly Asn Asp Gly Tyr
1               5

<210> SEQ ID NO 24
<211> LENGTH: 12
<212> TYPE: PRT
<213> ORGANISM: Artificial sequence
<220> FEATURE:
<223> OTHER INFORMATION: Synthetic polypeptide, Antibody G2 CDR L1

<400> SEQUENCE: 24

Ser Ala Ser Ser Ser Ile Ser Ser Ile Tyr Leu His
1               5                   10

<210> SEQ ID NO 25
<211> LENGTH: 7
<212> TYPE: PRT
<213> ORGANISM: Artificial sequence
<220> FEATURE:
<223> OTHER INFORMATION: Synthetic polypeptide, Antibody G2 CDR L2

<400> SEQUENCE: 25

Arg Ala Ser Asn Leu Ala Ser
1               5

<210> SEQ ID NO 26
<211> LENGTH: 9
<212> TYPE: PRT
<213> ORGANISM: Artificial sequence
<220> FEATURE:
<223> OTHER INFORMATION: Synthetic polypeptide, Antibody G2 CDR L3

<400> SEQUENCE: 26

Gln Gln Gly Ser Thr Ile Pro Phe Thr
1               5
```

<210> SEQ ID NO 27
<211> LENGTH: 345
<212> TYPE: DNA
<213> ORGANISM: Artificial sequence
<220> FEATURE:
<223> OTHER INFORMATION: Synthetic oligonucleotide, Antibody G2 heavy
      chain variable region

<400> SEQUENCE: 27
gaggtccagc tgcagcagtc tggacctgag ctggtaaagc ctggggcttc agtgaagatg      60
tcctgcaagg cttctggata cacattcact agctctgtta tgcactgggt gaagcagaag     120
cctgggcagg gccttgagtg gattggatat attaatcctt acaatgatgg tactaagtac     180
aatgagaagt tcaaaggcaa ggccacactg acttcagaca atcctccag cacagcctac      240 atggaactca gcagcctgac ctctgaggac tctgcggtct attactgtgc aaaggggggt     300
aacgatggct actggggcca aggcactact ctcacagtct cctca                     345

<210> SEQ ID NO 28
<211> LENGTH: 324
<212> TYPE: DNA
<213> ORGANISM: Artificial sequence
<220> FEATURE:
<223> OTHER INFORMATION: Synthetic oligonucleotide, Antibody G2 light
      chain variable region

<400> SEQUENCE: 28
gaaattgtgc tcacccagtc tccaaccacc atggctgcat ctcccgggga gaagatcact      60
atcacctgta gtgccagctc aagtataagt tccatttact tgcattggta tcagcagaag     120
ccaggattct ccctaaagt cttgatttat aggcatcca atctggcttc tggagtccca       180
gctcgcttca gtggcagtgg gtctgggacc tcttactctc tcacaattgg caccatggag     240
gctgaagatg ttgccactta ctactgccag cagggtagta ctataccatt cacgttcggc     300
tcggggacaa agttggaaat aaaa                                            324

<210> SEQ ID NO 29
<211> LENGTH: 216
<212> TYPE: PRT
<213> ORGANISM: Artificial sequence
<220> FEATURE:
<223> OTHER INFORMATION: Synthetic polypeptide, Antibody G2 heavy chain

<400> SEQUENCE: 29

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Ser
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Lys Gly Gly Asn Asp Gly Tyr Trp Gly Gln Gly Thr Thr Leu Thr
            100                 105                 110

Val Ser Ser Ala Lys Thr Thr Pro Pro Ser Val Tyr Pro Leu Ala Pro
        115                 120                 125

Gly Ser Ala Ala Gln Thr Asn Ser Met Val Thr Leu Gly Cys Leu Val
            130                 135                 140

Lys Gly Tyr Phe Pro Glu Pro Val Thr Val Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Ser Val Val Thr Val Pro Ser Ser Thr Trp Pro Ser
            180                 185                 190

Glu Thr Val Thr Cys Asn Val Ala His Pro Ala Ser Ser Thr Lys Val
            195                 200                 205

Asp Lys Lys Ile Val Pro Arg Asp
            210                 215

<210> SEQ ID NO 30
<211> LENGTH: 215
<212> TYPE: PRT
<213> ORGANISM: Artificial sequence
<220> FEATURE:
<223> OTHER INFORMATION: Synthetic polypeptide, Antibody G2 light chain

<400> SEQUENCE: 30

Glu Ile Val Leu Thr Gln Ser Pro Thr Thr Met Ala Ala Ser Pro Gly
1               5                   10                  15

Glu Lys Ile Thr Ile Thr Cys Ser Ala Ser Ser Ser Ile Ser Ser Ile
            20                  25                  30

Tyr Leu His Trp Tyr Gln Gln Lys Pro Gly Phe Ser Pro Lys Val Leu
        35                  40                  45

Ile Tyr Arg Ala Ser Asn Leu Ala Ser Gly Val Pro Ala Arg Phe Ser
50                  55                  60

Gly Ser Gly Ser Gly Thr Ser Tyr Ser Leu Thr Ile Gly Thr Met Glu
65                  70                  75                  80

Ala Glu Asp Val Ala Thr Tyr Tyr Cys Gln Gln Gly Ser Thr Ile Pro
                85                  90                  95

Phe Thr Phe Gly Ser Gly Thr Lys Leu Glu Ile Lys Arg Ala Asp Ala
            100                 105                 110

Ala Pro Thr Val Ser Ile Phe Pro Pro Ser Ser Glu Gln Leu Thr Ser
        115                 120                 125

Gly Gly Ala Ser Val Val Cys Phe Leu Asn Asn Phe Tyr Pro Arg Asp
130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
        195                 200                 205

Ser Phe Asn Arg Asn Glu Cys
210                 215

<210> SEQ ID NO 31
<211> LENGTH: 648
<212> TYPE: DNA
<213> ORGANISM: Artificial sequence
<220> FEATURE:
<223> OTHER INFORMATION: Synthetic oligonucleotide, Antibody G2 heavy
      chain

```
<400> SEQUENCE: 31
gaggtccagc tgcagcagtc tggacctgag ctggtaaagc ctggggcttc agtgaagatg        60
tcctgcaagg cttctggata cacattcact agctctgtta tgcactgggt gaagcagaag       120
cctgggcagg gccttgagtg gattggatat attaatcctt acaatgatgg tactaagtac       180
aatgagaagt tcaaaggcaa ggccacactg acttcagaca atcctccag cacagcctac        240 atggaactca gcagcctgac ctctgaggac tctgcggtct attactgtgc aaaaggggt        300 aacgatggct actggggcca aggcactact ctcacagtct cctcagccaa aacgacaccc       360
ccatctgtct atccactggc ccctggatct gctgcccaaa ctaactccat ggtgaccctg       420
ggatgcctgg tcaagggcta tttccctgag ccagtgacag tgacctggaa ctctggatcc       480
ctgtccagcg gtgtgcacac cttcccagct gtcctgcagt ctgacctcta cactctgagc       540
agctcagtga ctgtcccctc cagcacctgg cccagcgaga ccgtcacctg caacgttgcc       600
cacccggcca gcagcaccaa ggtggacaag aaaattgtgc ccagggat                    648

<210> SEQ ID NO 32
<211> LENGTH: 648
<212> TYPE: DNA
<213> ORGANISM: Artificial sequence
<220> FEATURE:
<223> OTHER INFORMATION: Synthetic oligonucleotide, Antibody G2 light
      chain

<400> SEQUENCE: 32
gaaattgtgc tcacccagtc tccaaccacc atggctgcat ctcccgggga gaagatcact        60
atcacctgta gtgccagctc aagtataagt tccatttact tgcattggta tcagcagaag       120
ccaggattct cccctaaagt cttgatttat agggcatcca atctggcttc tggagtccca       180
gctcgcttca gtggcagtgg gtctgggacc tcttactctc tcacaattgg caccatggag       240
gctgaagatg ttgccactta ctactgccag cagggtagta ctataccatt cacgttcggc       300
tcggggacaa agttggaaat aaaacgggct gatgctgcac caactgtatc catcttccca       360
ccatccagtg agcagttaac atctggaggt gcctcagtcg tgtgcttctt gaacaacttc       420
taccccagag acatcaatgt caagtggaag attgatggca gtgaacgaca aaatggtgtc       480
ctgaacagtt ggactgatca ggacagcaaa gacagcacct acagcatgag cagcaccctc       540
acattgacca aggacgagta tgaacgacat aacagctata cctgtgaggc cactcacaag       600
acatcaactt cacccatcgt caagagcttc aacaggaatg agtgttaa                    648
```

METHODS OF TREATING CHRONIC PAIN

RELATED APPLICATIONS

This application is a National Stage Application under 35 U.S.C. §371 of International Application No. PCT/IB2009/050852, filed on Mar. 3, 2009, which claims the benefit under 35 U.S.C. §119(e) of U.S. Provisional Patent Application No. 61/033,558, filed on Mar. 4, 2008, the entire contents of both are hereby incorporated by reference.

REFERENCE TO SEQUENCE LISTING

This application was filed electronically via EFS-Web and includes an electronically submitted sequence listing in .txt format. The .txt file contains a sequence listing entitled "PC33699A-SequenceListing-30Mar2011.txt", created on Mar. 30, 2011, and having a size of 26 KB. The sequence listing contained in this .txt file is part of the specification and is herein incorporated by reference in its entirety.

FIELD OF THE INVENTION

The invention relates to an anti-CGRP antibody for use in the prevention and/or treatment of chronic pain and/or symptoms of chronic pain, and to a method of treating and/or preventing chronic pain and/or symptoms of chronic pain using an anti-CGRP antibody.

BACKGROUND OF THE INVENTION

Chronic pain is a long lasting pain that persists longer than the temporal course of natural healing of the underlying causative injury or disease. It serves no beneficial or protective function and an estimated 2.7 million people in the UK are invalided due to chronic pain conditions.

Cancer pain is one of the most common types of chronic pain and demonstrates nociceptive components due to tumour growth and neuropathic components due to tumour induced nerve damage. It further involves structural damage, nerve entrapment and damage, inflammatory processes which lead to the disruption of normal tissue metabolism, the production of inflammatory prostaglandins and cytokines, and tissue damage.

To date, the main analgesics employed for treatment of chronic pain are opiates and non-steroidal anti-inflammatory drugs (NSAIDS). Both classes of drugs can produce severe side-effects; NSAIDS can cause gastric ulceration and renal damage, opiates can cause nausea, constipation, confusion and dependency problems. Opioids fail to produce pain relief in all individuals suffering chronic pain, even at high doses and development of analgesic resistance to opioids complicates their utility for long term therapy. In particular cancer pain treatment requires the use of unacceptably high levels of opiates bringing with it side-effects and at least 20% of treated patients still have uncontrolled pain.

Accordingly, there is a critical medical need to identify new pharmaceutically active compounds that interfere with key steps of the chronic pain process and particularly for the treatment and/or prevention of chronic nociceptive pain and/or symptoms of chronic nociceptive pain.

Surprisingly we have found that administration of an anti-CGRP antibody is effective, with a peripheral site of action, in the prevention and/or treatment of chronic pain and in particular chronic nociceptive pain such as cancer pain.

CGRP (calcitonin gene-related peptide) is a 37 amino acid neuropeptide which acts as a neurotransmitter in the central nervous system. It binds with high affinity to the CGRP receptor, Calcitonin receptor-like receptor (CRLR), activating adenylate cyclase and protein kinase A production.

Centrally penetrating spinally administered, small molecule selective CGRP antagonists have been shown to be useful in the treatment of neuropathic and nociceptive pain conditions (Adwanikar et al, Pain 2007) suggesting that removal of endogenous CGRP in the spinal cord has an antinociceptive effect. Additionally intrathecal administration of antiserum against CGRP has been shown to reduce nociceptive behaviour in rodent models of arthritis (Kuraishi, Y., et. al Neurosci. lett (1998) 92, 325-329).

Surprisingly we have found that administration of an anti-CGRP antibody is effective, with a peripheral site of action, in the prevention and/or treatment of chronic pain and in particular chronic nociceptive pain when administered peripherally. This peripheral administration route provides a distinct advantage over the requirement to administer antibodies intrathecally or spinally, a more high risk and inconvenient procedure.

BRIEF DESCRIPTION OF THE INVENTION

The present invention provides the use of an anti-CGRP antagonist antibody for the manufacture of a medicament for the prevention and/or treatment of chronic pain and/or symptoms of chronic pain, wherein the medicament is prepared to be peripherally administered.

The present invention further provides a method of prevention and/or treatment of chronic pain and/or symptoms of chronic pain, in an individual, which comprises peripherally administering to said individual a therapeutically effective amount of an anti-CGRP antagonist antibody.

In one embodiment, the anti-CGRP antagonist antibody acts peripherally on administration.

DESCRIPTION OF THE FIGURES

FIG. 8: CGRP sequences from human, cynomolgus monkey, rat, mouse, dog and rabbit. Non-conserved residues between species are underlined, the epitope of antibody G1 is in bold.

Figure 1:
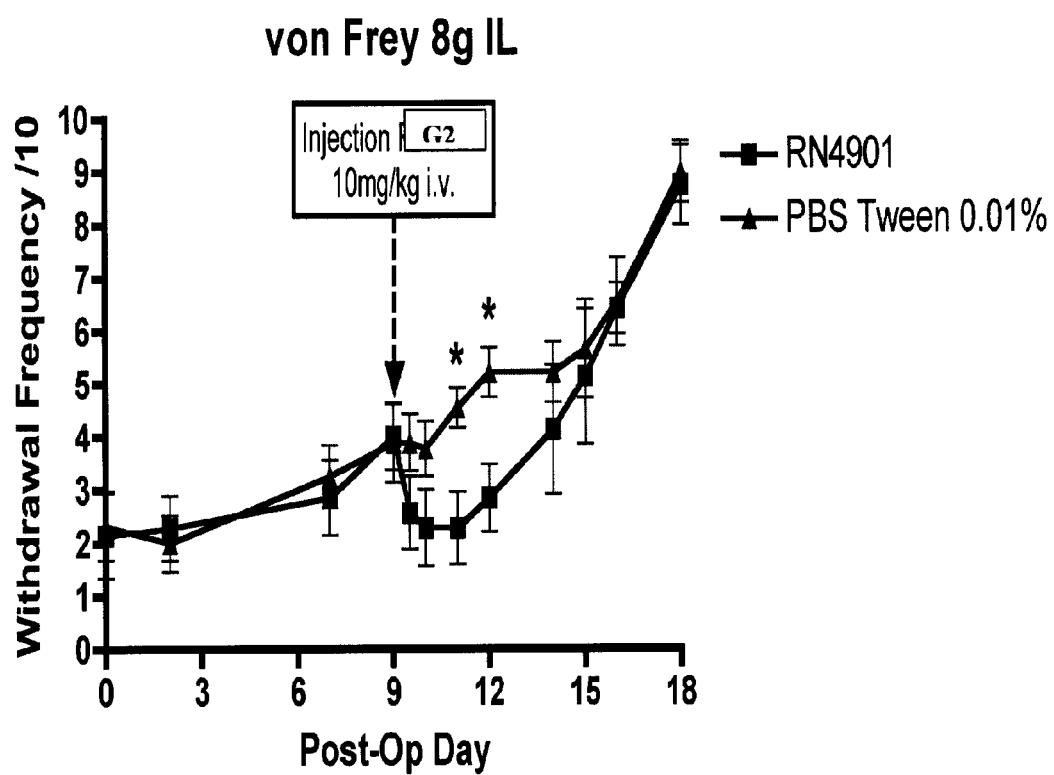
FIG. 1. Effect of antibody G2 on mechanical hypersensitivity to 8 gram von Frey stimuli in a bone cancer pain model. MRMT-1 injected rats were treated with antibody G2 or vehicle (PBS+0.01% Tween20) at day 9 post surgery. Groups were healthy throughout the post-operative period at all times, shown by increasing post-operative weight gain (data not shown). Data are mean±SEM of 7-9 rats per group. *$p<0.05$ versus vehicle treated group at each time point.

Table 1: Kd and IC50 of anti-CGRP antibodies measured at 25° C. against human α-CGRP [muMab7E9=murine precursor of G1. Its $K_D$ for rat β-CGRP=1 nM. RN4901=murine tool, recognising same epitope as G1 but showed same affinities and selectivity in rats (β-CGRP $K_D$=17 nM); G1=antibody humanized from muMab7E9 ($K_D$ for ratβ-CGRP=0.1 nM).]

Table 2: G1 binding affinities as determined by Biacore

DESCRIPTION OF THE INVENTION

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995); and Cancer: Principles and Practice of Oncology (V. T. DeVita et al., eds., J. B. Lippincott Company, 1993).

DEFINITIONS

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')$_2$, Fv, dAb), single chain antibodies (ScFv), mutants thereof, chimeric antibodies, diabodies, fusion proteins comprising an antibody portion, and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known "Fv" is an antibody fragment that contains a complete antigen-recognition and -binding site. In a two-chain Fv species, this region consists of a dimer of one heavy and one light chain variable domain in tight, non-covalent association. In a single-chain Fv species, one heavy and one light chain variable domain can be covalently linked by a flexible peptide linker such that the light and heavy chains can associate in a dimeric structure analogous to that in a two-chain Fv species. It is in this configuration that the three CDRs of each variable domain interact to define an antigen-binding specificity on the surface of the VH-VL dimer. However, even a single variable domain (or half of a Fv comprising only 3 CDRs specific for an antigen) has the ability to recognize and bind antigen, although generally at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge regions. A F(ab)2 fragment is a bivalent fragment comprising two Fab fragments linked by a disulfide bridge at the hinge region.

An antibody can have one or more binding sites (for combining with antigen). If there is more than one binding site, the binding sites may be identical to one another or may be different. For instance, a naturally-occurring immunoglobulin has two identical binding sites, a single chain antibody or Fab fragment has one binding site, while a "bispecific" or "bifunctional" antibody (diabody) has two different binding sites, in terms of sequence and/or antigen/epitope recognition.

An "isolated antibody" is an antibody that (1) is not associated with naturally-associated components, including other naturally-associated antibodies, that accompany it in its native state, (2) is free of other proteins from the same species, (3) is expressed by a cell from a different species, or (4) does not occur in nature.

A "monoclonal antibody" refers to a homogeneous antibody population wherein the monoclonal antibody is comprised of amino acids (naturally occurring and non-naturally occurring) that are involved in the selective binding of an antigen. A population of monoclonal antibodies is highly specific, being directed against a single antigenic site. The term "monoclonal antibody" encompasses not only intact monoclonal antibodies and full-length monoclonal antibodies, but also fragments thereof (such as Fab, Fab', F(ab')$_2$, Fv), single chain (ScFv), mutants thereof, fusion proteins comprising an antibody portion, and any other modified configuration of the immunoglobulin molecule that comprises an antigen recognition site of the required specificity and the ability to bind to an antigen. It is not intended to be limited as regards to the source of the antibody or the manner in which it is made (e.g., by hybridoma, phage selection, recombinant expression, transgenic animals, etc.).

As used herein, "humanized" antibodies refer to forms of non-human (e.g. murine) antibodies that are specific chimeric immunoglobulins, immunoglobulin chains, or fragments thereof (such as Fv, Fab, Fab', F(ab')2 or other antigen-binding subsequences of antibodies) that contain minimal sequence derived from non-human immunoglobulin. For the most part, humanized antibodies are human immunoglobulins (recipient antibody) in which residues from a complementarity determining region (CDR) of the recipient are replaced by residues from a CDR of a non-human species (donor antibody) such as mouse, rat, or rabbit having the desired specificity, affinity, and biological activity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody, which are also termed one or more CDRs "derived from" one or more CDRs from the original antibody.

As used herein, "human antibody" means an antibody having an amino acid sequence corresponding to that of an antibody produced by a human and/or has been made using any of the techniques for making human antibodies known in the art or disclosed herein. This definition of a human antibody includes antibodies comprising at least one human heavy chain polypeptide or at least one human light chain polypeptide. One such example is an antibody comprising murine light chain and human heavy chain polypeptides. Human antibodies can be produced using various techniques known in the art. In one embodiment, the human antibody is selected from a phage library, where that phage library expresses human antibodies (Vaughan et al., 1996, Nature Biotechnology, 14:309-314; Sheets et al., 1998, PNAS, (USA) 95:6157-6162; Hoogenboom and Winter, 1991, J. Mol. Biol., 227:381; Marks et al., 1991, J. Mol. Biol., 222:581). Human antibodies can also be made by introducing human immunoglobulin loci into transgenic animals, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from an individual or may have been immunized in vitro). See, e.g., Cole et al., Monoclonal Antibodies and Cancer Therapy, Alan R. Liss, p. 77 (1985); Boerner et al., 1991, J. Immunol., 147 (1):86-95; and U.S. Pat. No. 5,750,373.

A single chain antibody (scFc) is an antibody in which VL and VH regions are paired to form a monovalent molecule via a synthetic linker that enables them to be made as a single protein chain (Bird et al Science, 242: 423-426 (1988) and Huston et al., Proc. Natl. Acad. Sci. USA, 85:5879-5883 (1988)).

Diabodies are bivalent, bispecific antibodies in which VH and VL domains are expressed on a single polypeptide chain, but using a linker that is tooshort to allow for pairing between the two domains on the same chain, thereby forcing the domains to pair with complementary domains of another chain and creating two antigen binding sites.

"Chimeric antibodies" refers to those antibodies wherein one portion of each of the amino acid sequences of heavy and light chains is homologous to corresponding sequences in antibodies derived from a particular species or belonging to a particular class, while the remaining segment of the chains is homologous to corresponding sequences in another. Typically, in these chimeric antibodies, the variable region of both light and heavy chains mimics the variable regions of antibodies derived from one species of mammals, while the constant portions are homologous to the sequences in antibodies derived from another. One clear advantage to such chimeric forms is that, for example, the variable regions can conveniently be derived from presently known sources using readily available hybridomas or B cells from non human host organisms in combination with constant regions derived from, for example, human cell preparations. While the variable region has the advantage of ease of preparation, and the specificity is not affected by its source, the constant region being human, is less likely to elicit an immune response from a human subject when the antibodies are injected than would the constant region from a non-human source. However, the definition is not limited to this particular example.

A "functional Fc region" possesses at least one effector function of a native sequence Fc region. Exemplary "effector functions" include C1q binding; complement dependent cytotoxicity (CDC); Fc receptor binding; antibody-dependent cell-mediated cytotoxicity (ADCC); phagocytosis; down-regulation of cell surface receptors (e.g. B cell receptor; BCR), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification, yet retains at least one effector function of the native sequence Fc region. Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably at least about 90% sequence identity therewith, more preferably at least about 95% sequence identity therewith.

As used herein "antibody-dependent cell-mediated cytotoxicity" and "ADCC" refer to a cell-mediated reaction in which nonspecific cytotoxic cells that express Fc receptors (FcRs) (e.g. natural killer (NK) cells, neutrophils, and macrophages) recognize bound antibody on a target cell and subsequently cause lysis of the target cell. ADCC activity of a molecule of interest can be assessed using an in vitro ADCC assay, such as that described in U.S. Pat. No. 5,500,362 or 5,821,337. Useful effector cells for such assays include peripheral blood mononuclear cells (PBMC) and NK cells. Alternatively, or additionally, ADCC activity of the molecule of interest may be assessed in vivo, e.g., in a animal model such as that disclosed in Clynes et al., 1998, PNAS (USA), 95:652-656.

As used herein, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, 1991, Ann. Rev. Immunol., 9:457-92; Capel et al., 1994, Immunomethods, 4:25-34; and de Haas et al., 1995, J. Lab. Clin. Med., 126:330-41. "FcR" also includes the neonatal receptor, FcRn, which is responsible for the transfer of maternal IgGs to the fetus (Guyer et al., 1976, J. Immunol., 117:587; and Kim et al., 1994, J. Immunol., 24:249).

"Complement dependent cytotoxicity" and "CDC" refer to the lysing of a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., J. Immunol. Methods, 202:163 (1996), may be performed.

As used herein, the terms "G1" and "antibody G1" are used interchangeably to refer to an antibody produced by the expression vectors having deposit numbers ATCC-PTA-6867 and ATCC-PTA-6866. The amino acid sequence of the heavy chain and light chain variable regions are shown in SEQ ID Nos. 1 and 2. The CDR portions of antibody G1 (including Chothia and Kabat CDRs) are diagrammatically depicted in FIG. 5 of WO2007/054809, the content of which is herein incorporated by reference in its entirety. The polynucleotides encoding the heavy and light chain variable regions are shown in SEQ ID Nos., 9 and 10. The characterization of antibody G1 is described in the Examples of WO2007/054809, the entire content of which is herein incorporated by reference. G1 is a humanized monoclonal blocking antibody (IgG2) which blocks binding and activity of the neuropeptide CGRP (a and b) and its effect of neurogenic vasodilatation caused by CGRP release. G1 is an IgG2Δa monoclonal anti-CGRP antagonist antibody derived from the murine anti-CGRP antagonist antibody precursor, denoted muMAb7E9 as identified in a screen using spleen cells prepared from a mouse immunized with human and rat CGRP that were fused with murine plasmacytoma cells. G1 was created by grafting the muMAb 7E9 derived CDRs of light and heavy chain into the closest human germ line sequence followed by the introduction of at least 1 mutation into each CDR and 2 framework mutations in $V_H$. Two mutations were introduced into the Fc domain of G1 to suppress human Fc-receptor activation. G1 and muMab7E9 have been shown to recognise the same epitope.

As used herein, the terms "G2" and "antibody G2" are used interchangeably to refer to an anti-rat CGRP mouse monoclonal antibody as described in Wong H C et al. Hybridoma 12:93-106 (1993). The amino acid sequence of the heavy chain and light chain variable regions are shown in SEQ ID Nos. 19 and 20. The polynucleotides encoding the heavy and light chain variable regions are shown in SEQ ID Nos. 27 and 28. The CDR portions of antibody G2 are provided in SEQ ID Nos. 21 to 26. G2 has been shown to recognise the same epitope as G1.

As used herein, "immunospecific" binding of antibodies refers to the antigen specific binding interaction that occurs between the antigen-combining site of an antibody and the specific antigen recognized by that antibody (i.e., the antibody reacts with the protein in an ELISA or other immunoassay, and does not react detectably with unrelated proteins).

An epitope that "specifically binds", or "preferentially binds" (used interchangeably herein) to an antibody or a polypeptide is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

The terms "polypeptide", "oligopeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon an antibody, the polypeptides can occur as single chains or associated chains.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping groups moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Chothia et al. (1989) Nature 342:877; Al-lazikani et al (1997) J. Molec. Biol. 273:927-948)). As used herein, a CDR may refer to CDRs defined by either approach or by a combination of both approaches.

A "constant region" of an antibody refers to the constant region of the antibody light chain or the constant region of the antibody heavy chain, either alone or in combination.

As used herein, an "anti-CGRP antagonist antibody" (interchangeably termed "anti-CGRP antibody") refers to an antibody which is able to bind to CGRP and inhibit CGRP biological activity and/or downstream pathway(s). An anti-CGRP antagonist antibody encompasses antibodies that block, antagonize, suppress or reduce (including significantly) CGRP biological activity. For purpose of the present invention, it will be explicitly understood that the term "anti-CGRP antagonist antibody" encompass all the previously identified terms, titles, and functional states and characteristics whereby the CGRP itself, a CGRP biological activity, or the consequences of the biological activity, are substantially nullified, decreased, or neutralized in any meaningful degree. Examples of anti-CGRP antagonist antibodies are provided herein.

As used herein, "substantially pure" refers to material which is at least 50% pure (i.e., free from contaminants), more preferably at least 90% pure, more preferably at least 95% pure, more preferably at least 98% pure, more preferably at least 99% pure.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As used herein, "treatment" is an approach for obtaining beneficial or desired clinical results. For purposes of this invention, beneficial or desired clinical results include, but are not limited to, one or more of the following: improvement or alleviation of any aspect of chronic pain and/or symptom of chronic pain. For purposes of this invention, beneficial or desired clinical results include, but are not limited to, one or more of the following: including lessening severity, alleviation of pain and/or a symptom associated with chronic pain.

An "effective amount" of drug, compound, or pharmaceutical composition is an amount sufficient to effect beneficial or desired results including clinical results such as alleviation or reduction in pain sensation. An effective amount can be administered in one or more administrations. For purposes of this invention, an effective amount of drug, compound, or pharmaceutical composition is an amount sufficient to treat, ameliorate, reduce the intensity of and/or prevent chronic pain or symptom associated with chronic pain. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

In one embodiment, "prepared for" herein means the medicament is in the form of a dosage unit or the like suitably packaged and/or marked for use in peripheral administration.

"Reducing incidence" of chronic pain and/or a symptom associated with chronic pain means any of reducing severity (which can include reducing need for and/or amount of (e.g., exposure to) other drugs and/or therapies generally used for these conditions), duration, and/or frequency.

"Ameliorating" chronic pain and/or a symptom associated with chronic pain means a lessening or improvement of one or more symptoms of chronic pain and/or symptoms associated with chronic pain as compared to not administering an anti-CGRP antagonist antibody. "Ameliorating" also includes shortening or reduction in duration of a symptom.

"Palliating" chronic pain and/or a symptom associated with chronic pain means lessening the extent of one or more undesirable clinical manifestations of chronic pain in an individual or population of individuals treated with an anti-CGRP antagonist antibody in accordance with the invention.

As used therein, "delaying" the development of chronic pain means to defer, hinder, slow, retard, stabilize, and/or postpone progression of chronic pain and/or a symptom associated with chronic pain. This delay can be of varying lengths of time, depending on the history of the disease and/or individuals being treated. As is evident to one skilled in the art, a sufficient or significant delay can, in effect, encompass prevention, in that the individual does not develop chronic pain. A method that "delays" development of the symptom is a method that reduces probability of developing the symptom in a given time frame and/or reduces extent of the symptoms in a given time frame, when compared to not using the method. Such comparisons are typically based on clinical studies, using a statistically significant number of subjects.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides, or embedding in a semi-solid or solid matrix for sectioning purposes. The term "biological sample" encompasses a clinical sample, and also includes cells in culture, cell supernatants, cell lysates, serum, plasma, biological fluid, and tissue samples.

An "individual" or "subject" is a vertebrate, preferably a mammal, more preferably a human. Mammals include, but are not limited to, farm animals (such as cows), sport animals, pets (such as cats, dogs and horses), primates, mice and rats.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "pharmaceutically acceptable carrier" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000).

The term "peripherally administered" as used herein refers to the route by which the a substance, medicament and/or anti-CGRP antagonist antibody is to be delivered, in particular it means not centrally, not spinally, not intrathecally, not delivered directly into the CNS. The term refers to administration routes other than those immediately forgoing and includes via a route which is oral, sublingual, buccal, topical, rectal, via inhalation, transdermal, subcutaneous, intravenous, intra-arterial, intramuscular, intracardiac, intraosseous, intradermal, intraperitoneal, transmucosal, vaginal, intravitreal, intra-articular, peri-articular, local or epicutaneous.

The term "acts peripherally" as used herein refers to the site of action of a substance, compound, medicament and/or anti-CGRP antagonist antibody said site being within the peripheral nervous system as opposed to the central nervous system, said compound, medicament and/or anti-CGRP antagonist antibody said being limited by inability to cross the barrier to the CNS and brain when peripherally administered. The term "centrally penetrating" refers to the ability of a substance to cross the barrier to the brain or CNS.

The term "$K_{off}$", as used herein, is intended to refer to the off rate constant for dissociation of an antibody from the antibody/antigen complex.

The term "$K_d$", as used herein, is intended to refer to the dissociation constant of an antibody-antigen interaction.

The present invention is directed to a medicament for the prevention and/or treatment of chronic pain and/or symptoms of chronic pain and methods for prevention and/or treatment of chronic pain and/or symptoms of chronic pain in an individual.

In a first aspect, the invention provides the use of an anti-CGRP antagonist antibody for the manufacture of a medicament for the prevention and/or treatment of chronic pain and/or symptoms of chronic pain, wherein the medicament is prepared for peripheral administration or wherein the medicament is administered peripherally.

In a second aspect, the invention provides an anti-CGRP antagonist antibody for use in the prevention and/or treatment of chronic pain and/or symptoms of chronic pain wherein the antibody is prepared for peripheral administration or wherein the antibody is administered peripherally.

In third aspect, the invention provides the use of an anti-CGRP antagonist antibody for the manufacture of a medicament for ameliorating, controlling, reducing incidence of, or delaying the development or progression of chronic pain and/or symptoms of chronic pain, wherein the medicament is prepared for peripheral administration or wherein the medicament is administered peripherally. In the alternative of this aspect the invention provides an anti-CGRP antagonist antibody for use in ameliorating, controlling, reducing incidence of, or delaying the development or progression of chronic pain and/or symptoms of chronic pain, wherein the antibody is prepared for peripheral administration or wherein the antibody is administered peripherally.

In a fourth aspect, the invention provides a method of preventing and/or treating chronic pain and/or symptoms of chronic pain in an individual, comprising peripheral administration to the individual of an effective amount of an anti-CGRP antagonist antibody.

In a fifth aspect, the invention provides a method of ameliorating, controlling, reducing incidence of, or delaying the development or progression of chronic pain and/or symptoms of chronic pain in an individual, comprising peripheral administration to the individual of an effective amount of an anti-CGRP antagonist antibody.

According to a preferred embodiment of the present invention the individual is preferably a mammal, for example a companion animal such as a horse, cat or dog or a farm animal such as a sheep, cow or pig. Most preferably the mammal is a human.

According to a preferred embodiment of the present invention the medicament and/or anti-CGRP antagonist antibody is prepared for oral, sublingual, buccal, topical, rectal, inhalation, transdermal, subcutaneous, intravenous, intra-arterial, intramuscular, intracardiac, intraosseous, intradermal, intraperitoneal, transmucosal, vaginal, intravitreal, intra-articular, peri-articular, local or epicutaneous administration.

According to a further preferred embodiment the medicament is is prepared for peripheral administration prior to and/or during and/or after the development of chronic pain.

In one embodiment, the anti-CGRP antagonist antibody acts peripherally on administration. In one embodiment, the anti-CGRP antagonist antibody is not administered centrally, spinally or intrathecally.

According to a preferred embodiment of the present invention the chronic pain comprises one or more of chronic nociceptive pain, chronic neuropathic pain, chronic inflammatory pain, fibromyalgia, breakthrough pain and persistent pain. The chronic pain may comprise one or more of hyperalgesia, allodynia, central sensitisation, peripheral sensitisation, disinhibition and augmented facilitation.

According to a further preferred embodiment of the present invention the chronic pain is cancer pain, preferably cancer pain arising from malignancy or from cancer preferably selected from one or more of: adenocarcinoma in glandular tissue, blastoma in embryonic tissue of organs, carcinoma in epithelial tissue, leukemia in tissues that form blood cells, lymphoma in lymphatic tissue, myeloma in bone marrow, sarcoma in connective or supportive tissue, adrenal cancer, AIDS-related lymphoma, anemia, bladder cancer, bone cancer, brain cancer, breast cancer, carcinoid tumours, cervical cancer, chemotherapy, colon cancer, cytopenia, endometrial cancer, esophageal cancer, gastric cancer, head cancer, neck cancer, hepatobiliary cancer, kidney cancer, leukemia, liver cancer, lung cancer, lymphoma, Hodgkin's disease, lymphoma, non-Hodgkin's, nervous system tumours, oral cancer, ovarian cancer, pancreatic cancer, prostate cancer, rectal cancer, skin cancer, stomach cancer, testicular cancer, thyroid cancer, urethral cancer, bone cancer, sarcomas cancer of the connective tissue, cancer of bone tissue, cancer of blood-forming cells, cancer of bone marrow, multiple myeloma, leukaemia, primary or secondary bone cancer, tumours that metastasize to the bone, tumours infiltrating the nerve and hollow viscus, tumours near neural structures. Further preferably the cancer pain comprises visceral pain, preferably visceral pain which arises from pancreatic cancer and/or metastases in the abdomen. Further preferably the cancer pain comprises somatic pain, preferably somatic pain due to one or more of bone cancer, metastasis in the bone, postsurgical pain, sarcomas cancer of the connective tissue, cancer of bone tissue, cancer of blood-forming cells of the bone marrow, multiple myeloma, leukaemia, primary or secondary bone cancer.

According to a preferred embodiment of the present invention the anti-CGRP antagonist antibody binds to CGRP, more preferably binds to CGRP and inhibits the ability of CGRP to bind to the CGRP receptor. Preferably the anti-CGRP antagonist antibody binds to both human and rodent CGRP, preferably human and rat CGRP. More preferably the antibody binds to human CGRP, further preferably the anti-CGRP antagonist antibody binds to human α-CGRP or to human α-CGRP and/or β-CGRP. Most preferably the anti-CGRP antagonist antibody is an antibody that exhibits any one or more of the following functional characteristics: (a) binds to CGRP; (b) blocks CGRP from binding to its receptor(s); (c) blocks or decreases CGRP receptor activation, including cAMP activation; (d) inhibits, blocks, suppresses or reduces CGRP biological activity, including downstream pathways mediated by CGRP signalling, such as receptor binding and/or elicitation of a cellular response to CGRP; (e) prevents, ameliorates, or treats any aspect of chronic pain; (f) increases clearance of CGRP; and (g) inhibits (reduces) CGRP synthesis, production or release.

Antibodies of the invention, including G1 and G2, are known to bind CGRP and remove its biological availability for example in the serum thus preventing CGRP acces to the its receptor and downstream cellular responses and biological effects of CGRP such as flare and vasodilation.

In a further preferred embodiment of the invention the anti-CGRP antagonist antibody binds to a fragment of CGRP, more preferably to a fragment of CGRP as well as to the full length CGRP. Preferably, the anti-CGRP antagonist antibody binds to the C-terminal region or fragment of CRGP. The C-terminal region or fragment of CRGP preferably comprises amino acids 19-37 or 25-37 or 29-37 or alternatively 30-37, further alternatively 31-37 of CGRP. In a further embodiment, the C-terminal region or fragment of CRGP preferably comprises amino acids 32-37 most preferably 33 to 37 of CGRP. Preferably the CGRP is either α-CGRP or β-CGRP, further preferably human or rodent, further preferably human or rat, more preferably human, further preferably human α-CGRP or β-CGRP, most preferably human α-CGRP.

In a further preferred embodiment of the invention the anti-CGRP antagonist antibody specifically binds to the amino acid sequence GSKAF. Preferably the sequence GSKAF of CGRP is the epitope to which the anti-CGRP antagonist antibody binds, preferably at position 33 to 37, most preferably the sequence is GXXXF where X can be any amino acid, preferably at positions 33 to 37 of CGRP, the ends defined by amino acids G33 and F37 of CGRP.

In one embodiment, the present invention provides an anti-CGRP antagonist antibody which specifically binds to an epitope defined by amino acids G33 to F37 of CGRP. The anti-CGRP antagonist antibody may specifically bind to the epitope defined by the amino acid sequence GSKAF. In one embodiment, the present invention provides the use of such an antibody in the uses and methods defined in the various aspects of the present invention.

In one embodiment, the anti-CGRP antagonist antibody inhibits or prevents activation of the CGRP receptor. Preferably the anti-CGRP antibody has an IC50 of between 0.0001 (0.1 nM) to 500 µM. In some preferred embodiments, the IC50 is between 0.0001 µM and, or is at about, any of 250 µM, 100 µM, 50 µM, 10 µM, 1 µM, 500 nM, 250 nM, 100 nM, 50 nM, 20 nM, 15 nM, 10 nM, 5 nM, 1 nM, or 0.5 nM as measured in an in vitro binding assay. In some further preferred embodiments, IC50 is less than any of 500 pM, or 100 pM, or 50 pM, as measured in an in vitro binding assay. In a further more preferred embodiment IC50 is 1.2 nM or 31 nM.

In a further preferred embodiment, the anti-CGRP antagonist antibody used is capable of competing with an antibody herein above described for the binding of CGRP or to a fragment of CGRP, or to a fragment of CGRP as well as the full length CGRP, preferably to the C-terminal region or fragment of CRGP, preferably the C-terminal region or fragment of CRGP comprises amino acids 19-37 or 25-37 or 29-37 or alternatively 30-37, further alternatively 31-37 of CGRP. In a further embodiment, the C-terminal region or fragment of CRGP preferably comprises amino acids 32-37, most preferably 33 to 37 of CGRP.

In a further preferred embodiment, the anti-CGRP antagonist antibody or antigen binding portion thereof as used in the invention is an antibody capable of competing with an anti-CGRP antagonist antibody herein above described, in particular G1 or G2 as herein described, for:

(a) the binding of CGRP or a fragment of CGRP, or a fragment of CGRP as well as the full length CGRP, preferably the C-terminal region or fragment of CRGP, preferably the C-terminal region or fragment of CRGP comprising amino acids 19-37 or 25-37 or 29-37 or alternatively 30-37, further alternatively 31-37, preferably amino acids 32-37, most preferably 33 to 37 of CGRP, preferably the CGRP is alpha or beta, preferably beta, more preferably rodent or human, most preferably human, (b) the binding of the epitope sequence GSKAF, preferably at amino acid position 33 to 37 of CGRP as defined in (a), more preferably to the sequence GXXXF, where X is any amino acid, preferably GXXXF at amino acid position 33 to 37 of CGRP as defined in (a), (c) the binding as described in (a) or (b) with substantially the same Kd and/or substantially the same $K_{off}$, and/or (d) binding to CGRP and inhibiting/antagonising CGRP biological activity and/or downstream pathway(s), preferably the CGRP is alpha or beta, preferably beta, more preferably rodent or human, most preferably human.

The anti-CGRP antagonist antibody preferably binds to CGRP, region of CGRP or fragment of CGRP with a binding affinity ($K_d$) of between 0.000001 μM (0.001 nM) or 0.00001 μM (0.01 nM) to 500 μM. In some preferred embodiments, the binding affinity (Kd) is between 0.000001 μM or 0.00001 μM and, or is at about, any of 250 μM, 100 μM, 50 μM, 10 μM, 1 μM, 500 nM, 250 nM, 100 nM, 50 nM, 20 nM, 15 nM, 10 nM, 5 nM, 1 nM, 0.5 nM, 1 nM, 0.05 nM, or 0.01 nM, 0.005 nM, 0.001 nM, as measured in an in vitro binding assay. In some further preferred embodiments, binding affinity (Kd) is less than any of 500 pM, or 100 pM, 50 pM, or 10 pM, 5 pM, 1 pM, as measured in an in vitro binding assay. In a further more preferred embodiment binding affinity (Kd) is 0.04 nM or 16 nM.

The anti-CGRP antagonist antibody as used in the present invention may be selected from the group of: monoclonal antibodies, polyclonal antibodies, antibody fragments (e.g., Fab, Fab', F(ab')2, Fv, Fc, ScFv etc.), chimeric antibodies, bispecific antibodies, heteroconjugate antibodies, single chain (ScFv) antibodies, mutants thereof, fusion proteins comprising an antibody portion (e.g., a domain antibody), humanized antibodies, and any other modified configuration of the immunoglobulin molecule that comprises an antigen recognition site of the required specificity, including glycosylation variants of antibodies, amino acid sequence variants of antibodies, and covalently modified antibodies. The anti-CGRP antagonist antibody may be murine, rat, human, or any other origin (including chimeric or humanized antibodies). In some embodiments, the anti-CGRP antagonist antibody may be humanized but is more preferably human. Preferably the anti-CGRP antagonist antibody is isolated, further preferably it is substantially pure. Where the anti-CGRP antagonist antibody is an antibody fragment the fragment preferably retains the functional characteristics of the original antibody i.e. the CGRP binding and/or antagonist activity as described in the functional characteristics above.

Examples of anti-CGRP antagonist antibodies are known in the art. Hence according to a preferred embodiment of the present invention the anti-CGRP antagonist antibody as used in the present invention is preferably an anti-CGRP antibody as generally or specifically disclosed in any of (i) WO2007/054809, (ii) WO2007/076336, (iii) Tan et al., Clin. Sci. (Lond). 89:565-73, 1995, (iv) Sigma (Missouri, US), product number C7113 (clone #4901), (v) Plourde et al., Peptides 14:1225-1229, 1993 or which comprises or consists of:

(a) a fragment of said antibody (e.g., Fab, Fab', F(ab')2, Fv, Fc, ScFv etc.),
(b) a light chain of said antibody,
(c) a heavy chain of said antibody,
(d) one or more variable region(s) from a light chain and/or a heavy chain of said antibody,
(e) one or more CDR(s) (one, two, three, four, five or six CDRs) of said antibody,
(f) CDR H3 from the heavy chain of said antibody,
(g) CDR L3 from the light chain of said antibody,
(h) three CDRs from the light chain of said antibody,
(i) three CDRs from the heavy chain of said antibody,
(j) three CDRs from the light chain and three CDRs from the heavy chain, of said antibody,
(k) any one or more of (a) through (j).

According to a preferred embodiment of the present invention the anti-CGRP antagonist antibody is antibody G2 or antibody G1. According to a most preferred embodiment of the present the anti-CGRP antagonist antibody used is the anti-CGRP antibody G1 as specifically disclosed in the patent application WO2007/054809, or comprising its variants shown in Table 6 of WO2007/054809, also including functionally equivalent antibodies to G1, i.e. comprising conservative substitutions of amino acid residues or one or more deletions or additions of amino acids which do not significantly affect their functional characteristics e.g. CRGP binding or antagonist activity and variants which have enhanced or decreased activity and/or binding. As used herein, the terms "G1" and "antibody G1" are used interchangeably to refer to an antibody produced by expression vectors having deposit numbers of ATCC PTA-6867 and ATCC PTA-6866 as disclosed in application WO2007/054809.

According to a further embodiment of the present invention, the anti-CGRP antagonist antibody comprises or consists of a polypeptide selected from: (a) antibody G1 or its variants shown in Table 6 of WO2007/054809; (b) a fragment or a region of antibody G1 or its variants shown in Table 6 of WO2007/054809; (c) a light chain of antibody G1 or its variants shown in Table 6 of WO2007/054809; (d) a heavy chain of antibody G1 or its variants shown in Table 6 of WO2007/054809 (e) one or more variable region(s) from a light chain and/or a heavy chain of antibody G1 or its variants shown in Table 6 of WO2007/054809; (f) one or more CDR(s) (one, two, three, four, five or six CDRs) of antibody G1 or its variants shown in Table 6 of WO2007/054809; (g) CDR H3 from the heavy chain of antibody G1 or its variants shown in Table 6 of WO2007/054809; (h) CDR L3 from the light chain of antibody G1 or its variants shown in Table 6 of WO2007/054809; (i) three CDRs from the light chain of antibody G1 or its variants shown in Table 6 of WO2007/054809; (j) three CDRs from the heavy chain of antibody G1 or its variants shown in Table 6 of WO2007/054809; (k) three CDRs from the light chain and/or three CDRs from the heavy chain, of antibody G1 or its variants shown in Table 6 of WO2007/054809; and (i) an antibody comprising any one of (b) through (k). The invention also provides polypeptides comprising any one or more of the above. In some embodiments, the at least one, two, three, four, five, or six CDR(s) are at least about 85%, 86%, 87%, 88%, 89%, 90%, 95%, 96%, 97%, 98%, or 99% identical to at least one, two, three, four, five or six CDRs of G1 or its variants shown in Table 6 of WO2007/054809.

Determination of CDR regions is well within the ability of the skilled person. It is understood that in some embodiments, CDRs can be a combination of the Kabat and Chothia CDR. In some embodiments, the CDRs are the Kabat CDRs. In other embodiments, the CDRs are the Chothia CDRs.

The anti-CGRP antagonist antibody preferably comprises or consists of a fragment or a region of the antibody G1 (e.g., Fab, Fab', F(ab')2, Fv, Fc, ScFv etc.) or its variants shown in Table 6 of WO2007/054809. Preferably said fragment or region has the functional characteristics of an anti-CGRP antagonist antibody for example CGRP binding activity and/or antagonist activity and comprises or consists one or more of a light chain, heavy chain, fragment containing one or more variable regions from a light chain and/or a heavy chain, or one or more CDRs from a light chain and/or a heavy chain of the antibody G1.

According to a further preferred embodiment of the invention the anti-CGRP antagonist antibody comprises a light chain variable region, LCVR, comprising a peptide with a sequence selected from the group consisting of SEQ ID NOs: 28-32 and/or a heavy chain variable region, HCVR, comprising a peptide with a sequence selected from the group consisting of SEQ ID NOs: 34-38 of patent application WO2007/076336.

Further preferably the anti-CGRP antagonist antibody comprises an LCVR polypeptide of a SEQ ID NO as shown in Table 1 of patent application WO2007/076336 and further comprises a HCVR polypeptide of a SED ID NO as shown in Table 1 of patent application WO2007/076336.

According to a further embodiment of the invention the anti-CGRP antagonist antibody used comprises a light chain CDR (CDRL) selected from the group consisting of SEQ ID NOs: 8-13 and/or a heavy chain CDR (CDRH) selected from the group consisting of SEQ ID NOs: 14-22 of patent application WO2007/076336.

Methods of making and isolating the anti-CGRP antagonist antibodies of application WO2007/076336 and data demonstrating the CGRP binding and antagonist characterisation of the same are described in application WO2007/076336.

Preferably the anti-CGRP antagonist antibody for use in the present invention comprises a VH domain that is at least 85%, at least 86%, at least 87%, at least 88%, at least 89%, at least 90%, at least 91%, at least 92%, at least 93%, at least 94%, at least 95%, at least 96%, at least 97% at least 98%, at least 99% or 100% identical in amino acid sequence to SEQ ID NO: 1 or SEQ ID NO: 19 presented herein.

Preferably the anti-CGRP antagonist antibody comprises a VL domain that is at least 85%, at least 86%, at least 87%, at least 88%, at least 89%, at least 90%, at least 91%, at least 92%, at least 93%, at least 94%, at least 95%, at least 96%, at least 97% at least 98%, at least 99% or 100% identical in amino acid sequence to SEQ ID NO: 2 or SEQ ID NO: 20 presented herein.

The anti-CGRP antagonist antibody preferably comprises a VH domain and a VL domain that are at least 85%, at least 86%, at least 87%, at least 88%, at least 89%, at least 90%, at least 91%, at least 92%, at least 93%, at least 94%, at least 95%, at least 96%, at least 97% at least 98%, at least 99% or 100% identical in amino acid sequence to SEQ ID NO: 1 and 2 respectively or SEQ ID NO: 19 and 20 presented herein, respectively.

Preferably the anti-CGRP antagonist antibody comprises a VH domain that is at least 90% identical in amino acid sequence to SEQ ID NO: 1 and a VL domain that is at least 90% identical in amino acid sequence to SEQ ID NO: 2 presented herein.

Alternatively, the anti-CGRP antagonist antibody preferably comprises a VH domain that is at least 90% identical in amino acid sequence to SEQ ID NO: 19 and a VL domain that is at least 90% identical in amino acid sequence to SEQ ID NO: 20 presented herein.

The anti-CGRP antagonist antibody preferably comprises at least one CDR selected from the group consisting of: (a). CDR H1 as set forth in SEQ ID NO: 3 or 21; (b). CDR H2 as set forth in SEQ ID NO: 4 or 22; (c). CDR H3 as set forth in SEQ ID NO: 5 or 23; (d). CDR L1 as set forth in SEQ ID NO: 6 or 24; (e) CDR L2 as set forth in SEQ ID NO: 7 or 25; (f). CDR L3 as set forth in SEQ ID NO: 8 or 26; and (g). variants of CDR L1, CDR L2 and CDR H2 as shown in Table 6 of WO2007/054809.

According to a preferred embodiment of the present invention the anti-CGRP antagonist antibody heavy chain constant region may be from any types of constant region, such as IgG, IgM, IgD, IgA, and IgE; and any isotypes, such as IgGl, IgG2, IgG3, and IgG4.

Further preferably the anti-CGRP antagonist antibody comprises a heavy chain produced by the expression vector with ATCC Accession No. PTA-6867. Further preferably the anti-CGRP antagonist antibody comprises a light chain produced by the expression vector with ATCC Accession No. PTA-6866. Further preferably the anti-CGRP antagonist antibody is produced by the expression vectors with ATCC Accession Nos. PTA-6867 and PTA-6866.

Preferably the anti-CGRP antagonist antibody for use in the present invention is antibody G1 or antibody G2 defined herein.

According to a further embodiment of the invention, the anti-CGRP antagonist antibody comprises a modified constant region as for example described in WO2007/054809. Preferably the modified constant region is immunologically inert, including partially immunologically inert, such that it does not trigger complement mediated lysis, does not stimulate antibody-dependent cell mediated cytotoxicity (ADCC), does not activate microglia. Preferably the modified constant region is reduced in one or more of these activities. Most preferably the constant region is modified as described in Eur. J. Immunol. (1999) 29:2613-2624; PCT Application No. PCT/GB99/01441; and/or UK Patent Application No. 9809951.8. According to a preferred embodiment of the invention the anti-CGRP antagonist antibody comprises a human heavy chain IgG2 constant region comprising the following mutations: A330, P331 to S330, S331 (amino acid numbering with reference to the wildtype IgG2 sequence). Eur. J. Immunol. (1999) 29:2613-2624.

Methods of making and isolating the anti-CGRP antagonist antibodies of application WO2007/054809 and data demonstrating the CGRP binding and antagonist characterisation of the same are described in application WO2007/054809. Sequences of SEQ ID No. 1 to 14 of said application are provided herein as SEQ ID No. 1 to 14, respectively.

According to a further embodiment of the present invention the medicament is prepared for peripheral administration between once to 7 times per week, further preferably between once to four times per month, further preferably between once to six times per 6 month period, further preferably once to twelve times per year. Preferably the medicament is prepared to be peripherally administered in a period selected from: once daily, once every two, three, four, five or six days, weekly, once every two weeks, once every three weeks, monthly, once every two months, once every three months, once every four months, once every five months, once every six months, once every seven months, once every eight months, once every nine months, once every ten months, once every eleven months or yearly. According to preferred embodiments the medicament is prepared to be peripherally administered via a route selected from one or more of: orally, sublingually, buccally, topically, rectally, via inhalation, transdermally, subcutaneously, intravenously, intra-arterially or intramuscularly, via intracardiac administration, intraosseously, intradermally, intraperitoneally, transmucosally, vaginally, intravitreally, epicutaneously, intra-articularly, peri-articularly or locally.

According to a further embodiment of the present invention the medicament is prepared for peripheral administration with an antibody concentration of between 0.1 to 200 mg/ml; preferably at about, or between 0.1 and about, any one of 0.5, 1, 5, 10,15 20, 25, 30, 35, 40, 45, 50, 55, 60, 65, 70, 75, 80, 85, 90, 95, 100, 110, 120, 130, 140, 150, 160, 170, 180, 190 or 200 mg/ml +/−10% error, most preferably at 50 mg/ml.

According to a further embodiment of the present invention the medicament is prepared for peripheral administration with an antibody concentration of between 0.1 to 200 mg/kg of body weight; preferably at about, or between 0.1 and about, any one of 0.5, 1, 5, 10,15 20, 25, 30, 35, 40, 45, 50, 55, 60, 65, 70, 75, 80, 85, 90, 95, 100, 110, 120, 130, 140, 150, 160, 170, 180, 190 or 200 mg/kg of body weight +/−10% error, most preferably at 10 mg/kg.

According to a preferred embodiment of the present invention the anti-CGRP antagonist antibody has a half life in-vivo of more than any one of 2, 4, 6, 8,10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152,154, 156, 158, 160, 162, 164, 166, 168, 170, 172, 174, 176, 178, 180, 182, 184, 186, 188, 190, 192, 194, 196, 198, 200, 202, 204, 206, 208 or 210 days +/−1 day, further preferably more than any one of 7, 8, 9, 10, 11, or 12 months.

Preferably the anti-CGRP antagonist antibody has a half life in-vivo of more than 6 days.

According to a further preferred embodiment of the present invention, the medicament and/or the anti-CGRP antagonist antibody does not produce effects of central nervous system and/or cognitive impairment. Preferably the medicament and/or the anti-CGRP antagonist antibody does not induce any one ore more of the following: amnesia, confusion, depersonalization, hypesthesia, abnormal thinking, trismus, vertigo, akathisia, apathy, ataxia, circumoral paresthesia, CNS stimulation, emotional lability, euphoria, hallucinations, hostility, hyperesthesia, hyperkinesia, hypotonia, incoordination, libido increase, manic reaction, myoclonus, neuralgia, neuropathy, psychosis, seizure, abnormal speech, stupor, suicidal ideation; dizziness, somnolence, Insomnia, anxiety, tremor, depression or paresthesia. Most preferably the medicament and/or the anti-CGRP antagonist antibody does not induce impairment of motor coordination or attention.

According to a further embodiment of the present invention the medicament and/or the anti-CGRP antagonist antibody does not produce respiratory, renal or gastro-intestinal impairment.

According to a further embodiment of the present invention the medicament and/or the anti-CGRP antagonist antibody does not produce effects of physical and/or psychological dependence. Preferably the medicament and/or the anti-CGRP antagonist antibody does not demonstrate affinity for opiate, benzodiazepine, phencyclidine (PCP), or N-methyl-D-aspartic acid (NMDA) receptors, or CNS stimulant, or produce any sedating or euphoric effect.

In one embodiment, the anti-CGRP antagonist antibody, on administration, ameliorates, controls, reduces incidence of, or delays the development or progression of central pain sensation.

In another embodiment the effect of the anti-CGRP antagonist antibody is equal and/or superior to the effects of NSAIDS and/or opiates in the same models of chronic pain. In one embodiment, the anti-CGRP antagonist antibody is effective in treating refractory pain populations.

According to a further aspect of the present invention there is provided the use or method according to any other aspect of the invention wherein the anti-CGRP antagonist antibody is administered separately, sequentially or simultaneously in combination with one or more further pharmacologically active compounds or agents, preferably compounds or agents useful for treating chronic pain. Preferably the additional agent(s) is/are selected from one or more of:

(i) an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

(ii) a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin or zomepirac, cyclooxygenase-2 (COX-2) inhibitors, celecoxib; rofecoxib; meloxicam; JTE-522; L-745,337; NS398;, or a pharmaceutically acceptable salt thereof;

(iii) a barbiturate sedative, e.g. amobarbital, aprobarbital, butabarbital, butabital, mephobarbital, metharbital, methohexital, pentobarbital, phenobartital, secobarbital, talbutal, theamylal or thiopental or a pharmaceutically acceptable salt thereof;

(iv) a benzodiazepine having a sedative action, e.g. chlordiazepoxide, clorazepate, diazepam, flurazepam, lorazepam, oxazepam, temazepam or triazolam or a pharmaceutically acceptable salt thereof;

(v) an $H_1$ antagonist having a sedative action, e.g. diphenhydramine, pyrilamine, promethazine, chlorpheniramine or chlorcyclizine or a pharmaceutically acceptable salt thereof;

(vi) a sedative such as glutethimide, meprobamate, methaqualone or dichloralphenazone or a pharmaceutically acceptable salt thereof;

(vii) a skeletal muscle relaxant, e.g. baclofen, carisoprodol, chlorzoxazone, cyclobenzaprine, methocarbamol or orphrenadine or a pharmaceutically acceptable salt thereof;

(viii) an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinone or cis-4-(phosphonomethyl)-2-piperidinecarboxylic acid or a pharmaceutically acceptable salt thereof;

(ix) an alpha-adrenergic, e.g. doxazosin, tamsulosin, clonidine or 4-amino-6,7-dimethoxy-2-(5-methanesulfonamido-1,2,3,4-tetrahydroisoquinol-2-yl)-5-(2-pyridyl)quinazoline;

(x) a tricyclic antidepressant, e.g. desipramine, imipramine, amytriptiline or nortriptiline;

(xi) an anticonvulsant, e.g. carbamazepine or valproate;

(xii) a tachykinin (NK) antagonist, particularly an NK-3, NK-2 or NK-1 antagonist, e.g. (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]naphthridine-6-13-dione (TAK-637), 5-[[(2R,3S)-2-[(1R)-1-[3,5-bis (trifluoromethyl)phenyl]ethoxy-3-(4-fluorophenyl)-4- morpholinyl]methyl]-1,2-dihydro-3H-1,2,4-triazol-3-one (MK-869), lanepitant, dapitant or 3-[[2-methoxy-5-(trifluoromethoxy)phenyl]methylamino]-2-phenyl-piperidine (2S, 3S);
(xiii) a muscarinic antagonist, e.g oxybutin, tolterodine, propiverine, tropsium chloride or darifenacin;
(xiv) a COX-2 inhibitor, e.g. celecoxib, rofecoxib or valdecoxib;
(xv) a non-selective COX inhibitor (preferably with GI protection), e.g. nitroflurbiprofen (HCT-1026);
(xvi) a coal-tar analgesic, in particular paracetamol;
(xvii) a neuroleptic such as droperidol;
(xviii) a vanilloid receptor agonist (e.g. resinferatoxin) or antagonist (e.g. capsazepine);
(xix) a beta-adrenergic such as propranolol;
(xx) a local anaesthetic, such as mexiletine;
(xxi) a corticosteriod, such as dexamethasone;
(xxii) a serotonin receptor agonist or antagonist;
(xxiii) a cholinergic (nicotinic) analgesic;
(xxiv) Tramadol (trade mark);
(xxv) a PDEV inhibitor, such as sildenafil, vardenafil or taladafil;
(xxvi) an alpha-2-delta ligand such as gabapentin or pregabalin;
(xxvii) a canabinoid; and
(xxviii) an antidepressant, such as amitriptyline (Elavil), trazodone (Desyrel), and imipramine (Tofranil) or anticonvulsants such as phenytoin (Dilantin) or carbamazepine (Tegretol).

According to a further aspect of the present invention there is provided a pharmaceutical composition for the prevention and/or treatment of chronic pain and/or symptoms of chronic pain or for ameliorating, controlling, reducing incidence of, or delaying the development or progression of chronic pain and/or symptoms of chronic pain in an individual, comprising an anti-CGRP antagonist antibody and a pharmaceutically acceptable carrier and/or an excipient, wherein the composition is prepared to be peripherally administered.

According to a further aspect of the present invention there is provided a kit comprising:
(a) a pharmaceutical composition as defined above; and
(b) instructions for the peripheral administration of an effective amount of said pharmaceutical composition to an individual for the prevention and/or treatment of chronic pain and/or symptoms of chronic pain or for ameliorating, controlling, reducing incidence of, or delaying the development or progression of chronic pain and/or symptoms of chronic pain.

The kit may include one or more containers containing an anti-CGRP antagonist antibody or polypeptide described herein and instructions for use in accordance with any of the methods and uses of the invention. The kit may further comprise a description of selecting an individual suitable for treatment based on identifying whether that individual has chronic pain or is at risk of having chronic pain. The instructions for the peripheral administration of the pharmaceutical composition may include information as to dosage, dosing schedule and routes of administration for the intended treatment.

Preferred features of each aspect of the invention apply equally to each other aspect mutatis mutandis.

EXAMPLES

The present invention is now described with reference to the following Examples which are intended to illustrate but not to limit the invention.

The following examples and figures are made with reference to antibody G1, an anti-human CGRP human monoclonal antibody; and to antibody G2, an anti-rat CGRP mouse monoclonal antibody (Wong H C et al. Hybridoma 12:93-106 (1993)).

Example 1

Set Up of the Rodent Cancer Mechanistic Pain Model

Tumour cells used are syngeneic MRMT-1 rat mammary gland carcinoma cells donated from the Novartis Institute (London). The cells are cultured in RPMI 1640 (Gibco) with 10% foetal bovine serum (FCS), 1% L-glutamine 2% penicillin/streptomycin (Gibco). Two brief washes are carried out with 0.1% w/v trypsin to release those cells which adhere to the flask, and then quenched with an equal volume of 10% FCS, followed by centrifugation of the solution for 3 minutes at 1200 rpm. The pellet is washed and resuspended in Hanks medium, and the concentration of cells calculated using a Haemocytometer, with trypan blue staining to determine the number of dead MRMT-1 cells. The final concentration of $3 \times 10^3$ cells was then obtained by diluting the solution according to the number of cells seen. The final solution was kept on ice until time of injection.

Male Sprague-Dawley rats weighing close to 170 g at time of surgery were used to generate the cancer model. Anaesthesia was induced in the rats using halothane or isoflurane (1.5-2%) 66% $N_2O$ and 33% $O_2$, the leg was shaved over the appropriate area and disinfected with chlorhexidine (Animalcare Ltd, UK.). A small incision in order to expose the anterior-medial surface of the distal end of the tibia was made. A hole was bored in the periosteum using a 0.7 mm dental drill, through which a 2 cm polythene tubing was fed 1 cm into the intra-medullar cavity of the tibia. Using a Hamilton syringe the pre-prepared 10 µl of $3 \times 10^3$ MRMT-1 cells were injected through the tubing into the cavity. The tubing was then removed and the hole plugged using bone restorative material (IRM, Dentsply USA). The wound was then irrigated with 0.9% saline and closed with a metal clip. The sham animals were operated upon using the same procedure but injected with 10 µl of Hank's solution alone. The animals were placed in a thermoregulated recovery box until such time that they were able to be placed back in their housing cages.

Example 2

Assessment of Rodent Anti-CGRP Antibody G2 in the Cancer Pain Model

Testing behaviour towards mechanical stimuli uses von Frey filaments (North Coast Medical Inc., USA) to the plantar surface of both the ipsilateral and contralateral hindpaw. The rats were placed in a Perspex cubicle with a mesh floor and allowed to acclimatise for 10 minutes. Each von Frey was applied 10 times to each hindpaw alternating between the ipsilateral and contralateral, for duration of 2-3 seconds each time. Von Frey Filaments used have bending forces of 1, 5, 9 and 15 g, and a period of 5 minutes was left between ascending von Frey forces. A nocifensive response (a lift) is defined as a brisk withdrawal of the hindpaw and the number of lifts for each paw at each von Frey are recorded (maximum of 10) and expressed as a percentage response.

An assessment of the efficacy of rodent anti-CGRP antibody G2 in attenuating hypersensitivity to a wide variety of static mechanical, cooling and integrated stimuli was carried out as well as the background basal pain behaviours in this validated model of cancer induced bone pain. The responses measured are attenuated by standard analgesic treatments such as morphine and gabapentin. All measures were made by the same scientist in a blind fashion—blinded to the identity of the compound/control and to the treatment of the animal.

G2-was given IV at 10 mg/kg at day 9 and rats were tested at 2 hrs and then on days 10, 11, 12 and then 14-18 days post treatment (FIG. 1).

G2 had marked effect on the behavioural responses to the higher intensity mechanical stimuli. Withdrawal frequencies to von Frey 8 g were reduced two hours after injection and were significantly reduced over that seen in the vehicle treated group on days 11 and 12 (days 2 and 3 after injection, p=0.0164 and 0.0311, respectively). In fact, the G2 treated animals now had pain scores similar to the baseline values. By day 14 (day 5 post-G2 injection) there was no discernible difference between the G2 and vehicle-treated groups. Both groups reached a similar level of hypersensitivity to von Frey 8 g by day 18 after MRMT-1 injection (day 9 post-treatment).

Figure 2:
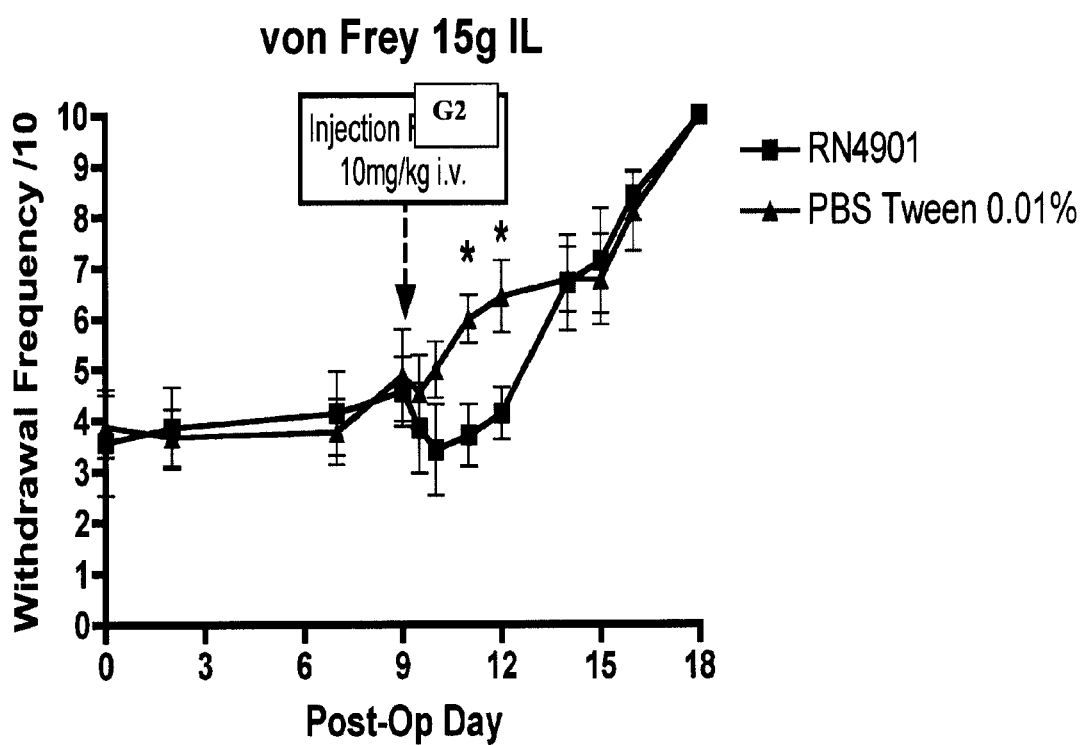
FIG. 2. Effect of antibody G2 on mechanical hypersensitivity to 15 gr von Frey stimuli in the bone cancer pain model. MRMT-1 injected rats were treated with G2or vehicle (PBS+0.01% Tween20) at day 9 post surgery. Data are mean±SEM of 7-9 rats per group. *$p<0.05$ versus vehicle treated group at each time point.

A similar reversal in hypersensitivity to von Frey 15 g was also apparent. A reduction in hypersensitivity to von Frey 15 g from vehicle treated group was evident at 2 hours post-injection with significance seen at 2 and 3 days after drug administration (p=0.02 and 0.03 respectively). The reductions were lost by 6 days after G2 administration and both groups now reached similar maximal withdrawal frequencies by 18 days post MRMT-1 injection (FIG. 2).

The results indicate that G2 reduces noxious pain experienced in the metastatic bone cancer rat model.

Example 3

Rota Rod Test for Motor Impairment

Figure 3:
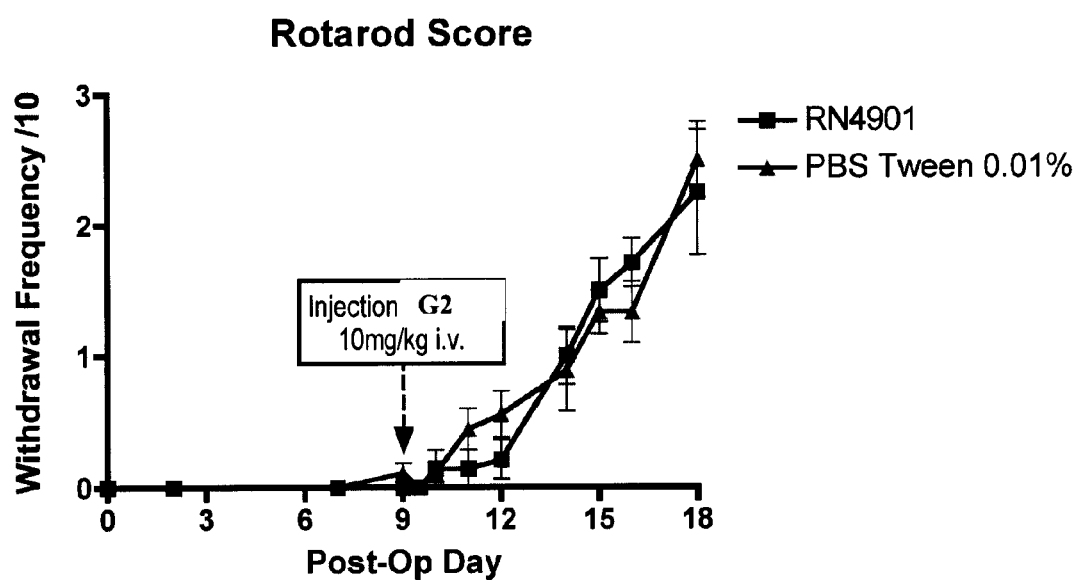
FIG. 3. Effect of antibody G2 on ambulation measured by rota rod. Two end points were explored. The latency to fall as measurements of compound induced impairments in motor co-ordination (A), and rota rod score, as measurements of ambulation evoked pain (B) in the bone cancer pain model. MRMT-1 injected rats were treated with antibody G2 or vehicle (PBS+0.01% Tween20) at day 9 post surgery. Data are mean±SEM of 7-9 rats per group. *$p<0.05$ versus vehicle treated group at each time point.

A further end point tested in the bone cancer pain model was ambulation (by rotarod). The test is to obtain a measurement of locomotor impairment comparing antibody treated with control animals, each subjected to the same test under the same conditions. The rota rod test consists of 4 rotateable drums divided by flanges with a motor-driven drum accelerated (Ugo Basile, Comerio, VA, Italy). For a given trial, a rat is placed on the rotating rod and the rotation speed is accelerated from 4 to 16 rpm in 2 min. The time of maximal performance is typically set at 120 sec. Each animal generally receives three trials per day, at 1 hr intervals, for several consecutive days post surgery. The latency to fall off the rod is represented as mean of the three trials. No differences were found between the antibody G2 group and the vehicle group in the latency to fall from the rotarod during forced ambulation (FIG. 3). This suggests that G2 does not impair pathways involved in motor co-ordination, or attention and points to a lack of CNS side-effects produced by the antibody.

Example 4

Binding Assay

Figure 4:
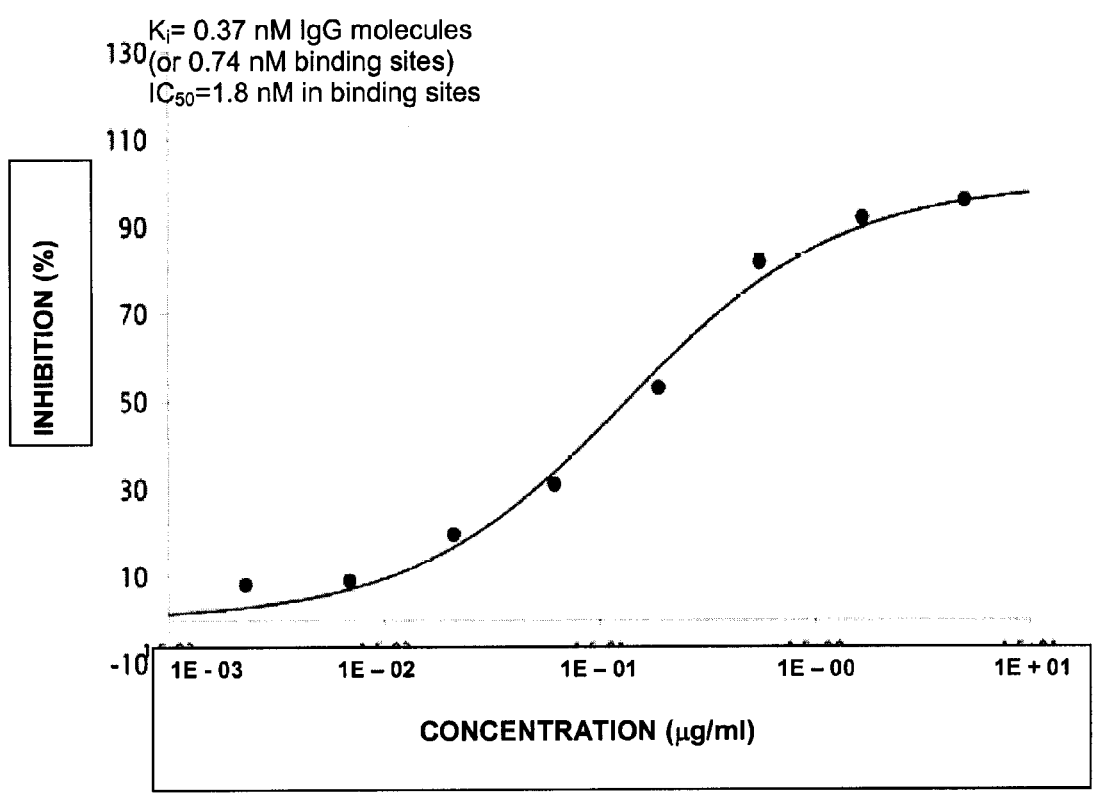
FIG. 4: Binding assay data demonstrating antibody G1 inhibits the binding of α-CGRP to the CGRP1 receptor.

A binding assay was performed to measure the $IC_{50}$ of anti-CGRP antibody G1 and G2 in blocking human α-CGRP from binding to the CGRP1-receptor in SK-N-MC cells. Dose response curves were plotted and $K_i$ values were determined using the equation: $K_i = IC_{50}/(1+([ligand]/K_D))$; FIG. 4, where the equilibrium dissociation constant $K_D$=8 pM for human α-CGRP to CGRP1-receptor as present in SK-N-MC cells. The reported $IC_{50}$ value (in terms of IgG molecules) was converted to binding sites so that it could be compared with the affinities ($K_D$) determined by Biacore, using N-biotinylated human and rat α-CGRPs were captured on individual flow cells at low levels (typically 100 response units) to provide the reaction surfaces, while an unmodified flow cell served as a reference channel. G1 was titrated over the chip surface Binding affinities were deduced from the quotient of the kinetic rate constants ($K_D=k_{off}/k_{on}$) see Table 1.

TABLE 1

|  | G2 | Mouse Mab 7E9 | G1 |
| --- | --- | --- | --- |
| KD (nM), α-Hu | 17 | 1.0 | 0.04 |
| IC50 (nM) α-Hu | 37 | 2.6 | 1.2 |
| KD (nM) α-Rat | 1.0 | 58 | 1.2 |

TABLE 2

| N-biotin-CGRP on chip | °C. | $k_{on}$ (1/Ms) | $k_{off}$ (1/s) | $T_{1/2}$ (h) | $K_D$ (nM) |
| --- | --- | --- | --- | --- | --- |
| α-human | 25 | $1.86 \times 10^5$ | $7.80 \times 10^{-5}$ | 24.68 | 0.042 |
| α-humam | 37 | $5.87 \times 10^5$ | $3.63 \times 10^{-5}$ | 5.30 | 0.063 |
| β-human | 37 | $4.51 \times 10^5$ | $6.98 \times 10^{-5}$ | 2.76 | 0.155 |
| α-rat | 25 | $5.08 \times 10^4$ | $6.18 \times 10^{-5}$ | 3.12 | 1.22 |
| α-rat | 37 | $1.55 \times 10^5$ | $3.99 \times 10^{-4}$ | 0.48 | 2.57 |
| β-rat | 37 | $5.16 \times 10^5$ | $7.85 \times 10^{-5}$ | 2.45 | 0.152 |

Binding affinity of G1 for human α and β CGRP was equivalent (Kd=0.155 and 0.152 nM respectively). Binding affinity of G2 for rat α and β CGRP was equivalent (16 and 17 nM, respectively). Additionally G1 binding affinity is 40-fold more potent in human than rat for α-CGRP (Kd=0.042 and 1.22 nM, respectively) and equi-potent in human and rat for β-CGRP (Kd=0.155 and 0.152 nM, respectively). Antibody G1 also demonstrated good cross species selectivity and binds rat α-CGRP with the same affinity as antibody G2 (around 1.2 nM) Table 2.

G1 binds human and cynomolgus monkey α- and β-CGRP with high affinity ($K_D$=63 and 155 pM, respectively). G1 displays species selectivity for human/cyno CGRP and binds α- and β-CGRP from other species e.g. rat with lower affinity ($K_D$=2.57 nM and 152 pM, respectively).

Example 5

Half Life of Anti-CGRP In-Vivo

Figure 5A:
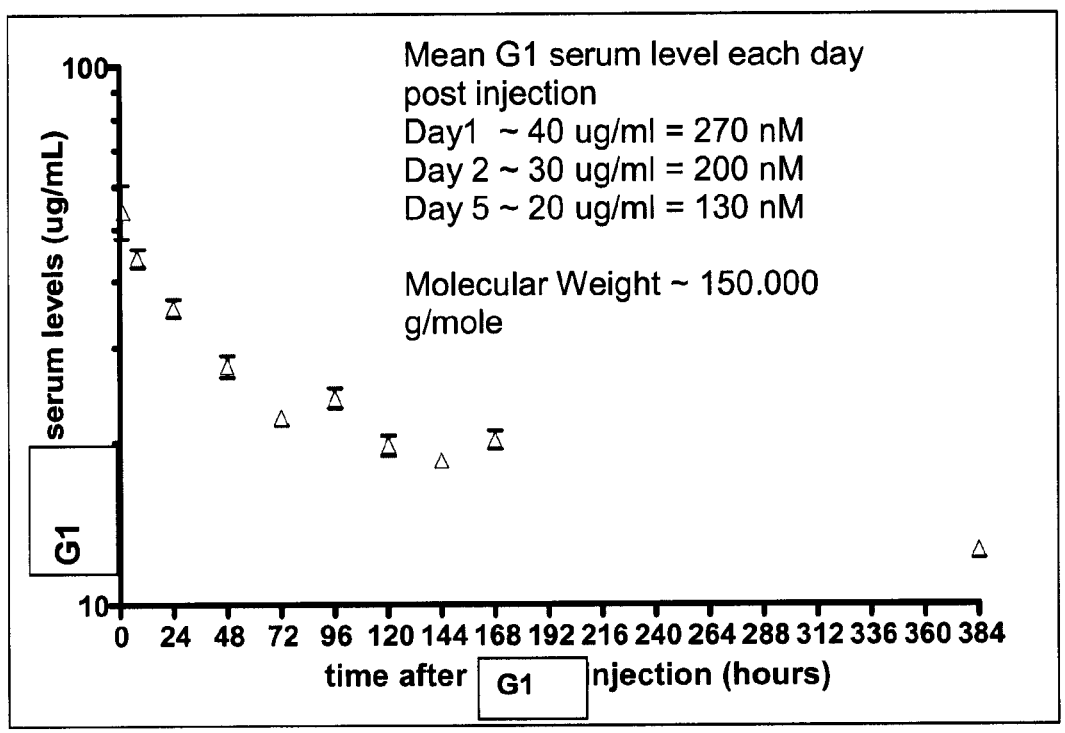
FIG. 5a: serum level of anti-CGRP concentration (ug/ml) vs time after IV administration of 10 mg/kg, measured by anti-IgG ELISA.
Figure 5B:
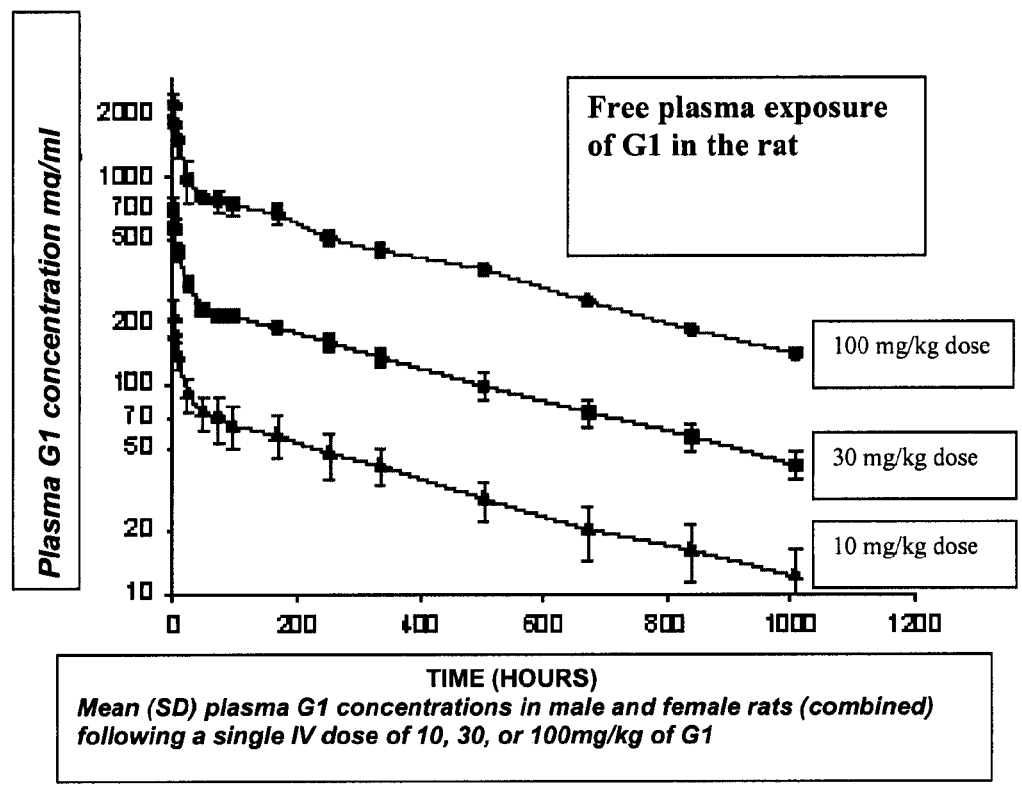
FIG. 5b: serum level of anti-CGRP concentration (ug/ml) vs time after IV administration of 10, 30, 100 mg/kg, measured by anti-IgG ELISA.

Serum measurements of anti-CGRP in rat, FIG. 5, indicate that the half life is of the order of 7 days. The antibody is peripherally restricted having a molecular weight of around 150,000, FIGS. 5a, 5b, i.e. it does not cross into the central nervous system or cross the blood brain barrier.

Example 6

Selectivity of Anti-CGRP Antibody

Figure 7:
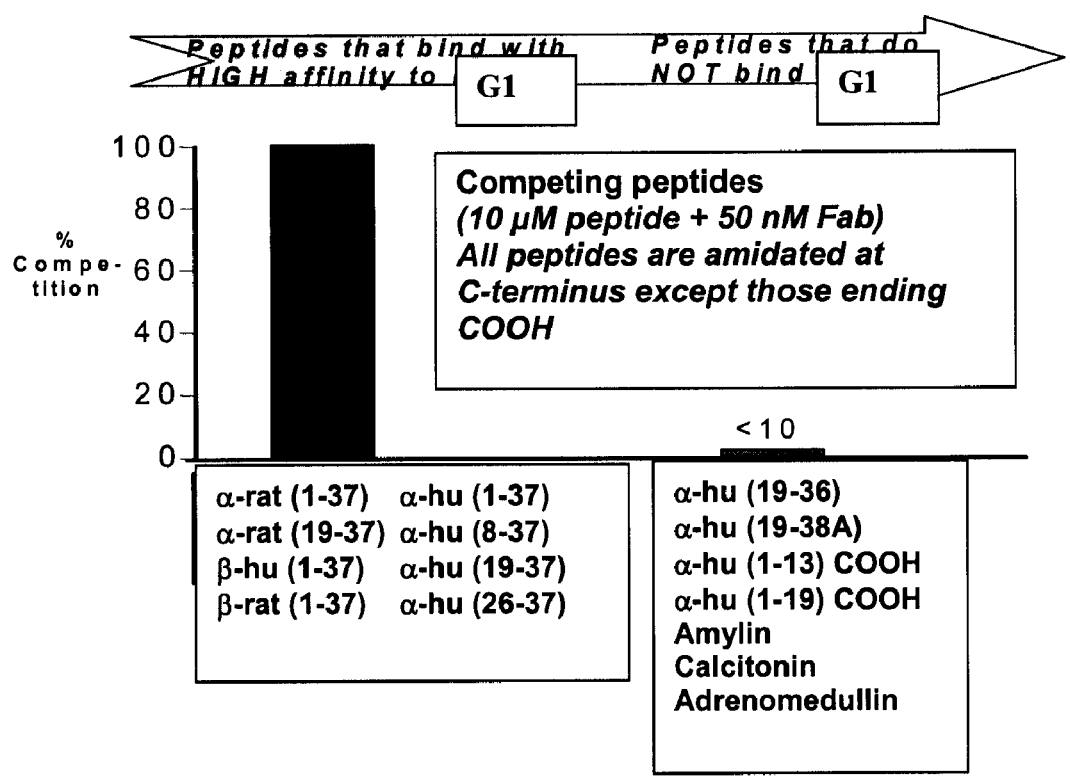
FIG. 7: Solution competition by Biacore: CGRP, CGRP fragments or peptides related in sequence to CGRP were used to determine the specificity of antibody G1.

We determined the specificity of antibody G1 to human or rat CGRP by using the Biacore chip to "probe" the free concentration of a premixed complex of mAb+peptide. As expected when we pre-incubated antibody G1 with human or rat CGRP the response was fully blocked. In contrast pre-incubating G1, with an excess of amylin, calcitonin or adrenomedullin was comparable to the control response (G1 plus buffer) demonstrating that G1 did not form a complex with these peptides (FIG. 7).

Example 7

Identification of Antibody G1 Binding Epitope

Interaction analysis was conducted at 25° C. on a Biacore 3000™ system equipped with streptavidin-coated (SA) sensor chips (Biacore AB, Uppsala, Sweden) using a standard Biacore running buffer (HBS-P). First we confirmed that an N-biotinylated 25-37 human α-CGRP fragment bound with the same affinity to antibody G1, as full-length N-biotinylated human α-CGRP. Each amino acid between position 27-37 was then mutated individually to alanine and expressed the fold loss in affinity compared to the wild-type fragment. N-biotinylated fragments were captured on individual flow cells at low levels (typically 100 response units) to provide the reaction surfaces, while an unmodified flow cell served as a reference channel. Purified Fab fragments of antibody G1 were generated. Fab fragments were titrated over the chip using 1 µM as the top concentration of a two-fold dilution series. Association and dissociation phases were monitored at 100 µl/min for 1 minute and 5 minutes respectively. Surfaces were regenerated with a mixture of 35% ethanol+25mM NaOH+0.5M NaCl.

Figure 6:
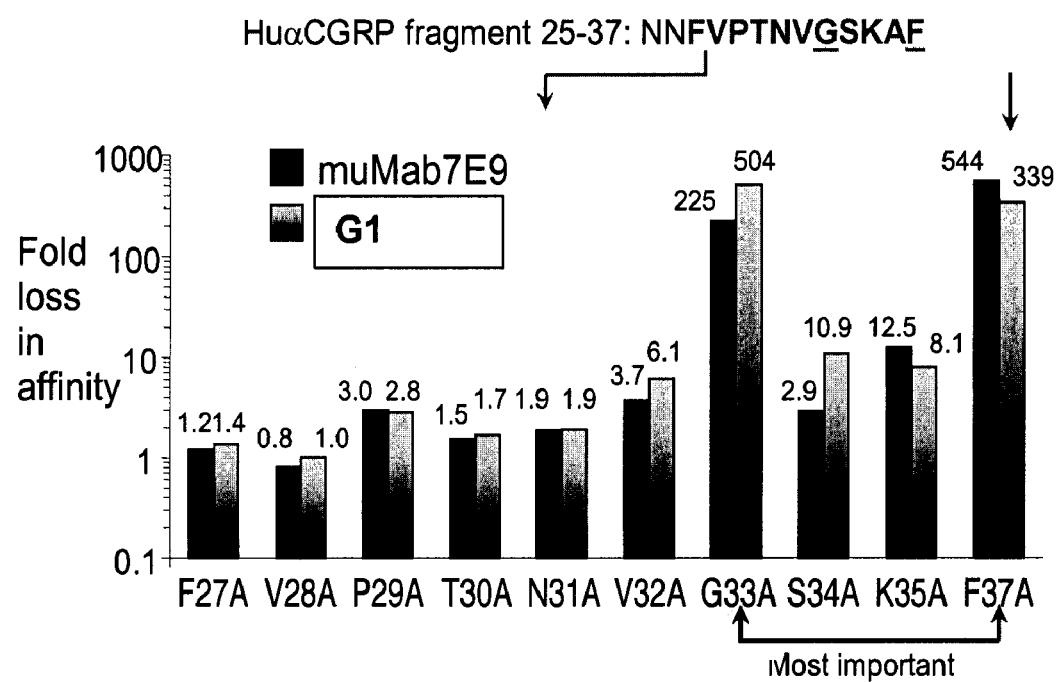
FIG. 6 Alanine scan using a C-terminal CGRP fragment (CGRP 25-37). The change in affinity is expressed in fold loss of affinity and which shows that anti-CGRP antibody G1 binds to the C-terminal region of human α-CGRP.

The alanine scan results show that antibody G1 binds to the C-terminal region of human α-CGRP, particularly residues 25 to 37, and shows specific binding to a region (i.e. loss of affinity is markedly increased when the specific binding region is mutated) which can be defined as the epitope and which lies within the last 5 C-terminal amino acids, i.e. from G33A to F37A. Most profound changes in affinity are caused through the G33A and F37A mutation (FIG. 6). C-terminal Phe is important for selectivity of antibody G1 for CGRP vs related peptides and gene family members (FIG. 8).

Thus, in one embodiment, the present invention provides an anti-CGRP antagonist antibody which specifically binds to an epitope defined by amino acids G33 to F37 of CGRP. The anti-CGRP antagonist antibody may specifically bind to the epitope defined by the amino acid sequence GSKAF, more specifically to the epitope of CGRP is defined as GXXXF where X can be any amino acid, the G33 and F37 being the most important residues of the epitope for defining high affinity binding of the anti-CGRP antagonist antibody.

Example 8

Analysis of Indicators of Physical or Psychological Dependence

Neither antibody G1 nor antibody G2 demonstrate CNS penetration. Additionally long term observation of animals (rats) dosed with either antibody to levels used in the previous examples did not reveal adverse CNS events such as sedation or stimulation/euphoric behaviour in comparison to control animals. These observations indicate an absence of dependency risk for the antibodies and hence a significantly improved safety of the antibodies over current opiates used in current pain therapies.

Example 9

Analysis of Indicators of Gastro-Intestinal Adverse Effects

A 1 month in-vivo rat study with antibody G2 and 1 week comparative study with antibody G1 demonstrated that no adverse gastro intestinal effects were observed on behaviour, food intake, stool production or histopathology in comparison to control animals. These observations indicate an absence of gastrointestinal risk for the antibodies and hence a significantly improved safety of the antibodies over current NSAIDs used in current pain therapies.

Example 10

G1 and G2 as Anti-CGRP Antagonist Antibodies

A known consequence of CGRP biological activity is the generation neurogenic flare when delivered in vivo. G1 and G2 are demonstrated to be anti-CGRP antagonist antibodies in that they prevent the development of neurogenic flare in vivo.

Using a neurogenic skin flare rat model the efficacy of G1 was tested for its ability to block CGRP effect in vivo. The saphenous nerve in the rat is electrically stimulated causing CGRP release from nerve endings and leading to vasodilation, the resulting changes in blood flow can be measured using laser Dopler methods.

Changes in blood flow parameters were expressed as the area under the curve (AUC, change in arbitrary Doppler flux units multiplied by time). CGRP receptor antagonist $CGRP_{8-37}$ (400 nmol/kg, i.v.) was used as a positive control to validate the specificity of the model (data not shown). To determine the effect of G1 prior to dosing for each animal, the baseline blood flow response to stimulation was established with two saphenous nerve stimulations each 30 minutes apart. Rats were treated with G1 after the blood flow response of the second stimulation had returned to baseline levels (approximately 10 minutes post stimulation) and an additional four stimulations at 30 minute intervals were performed.

Figure 9:
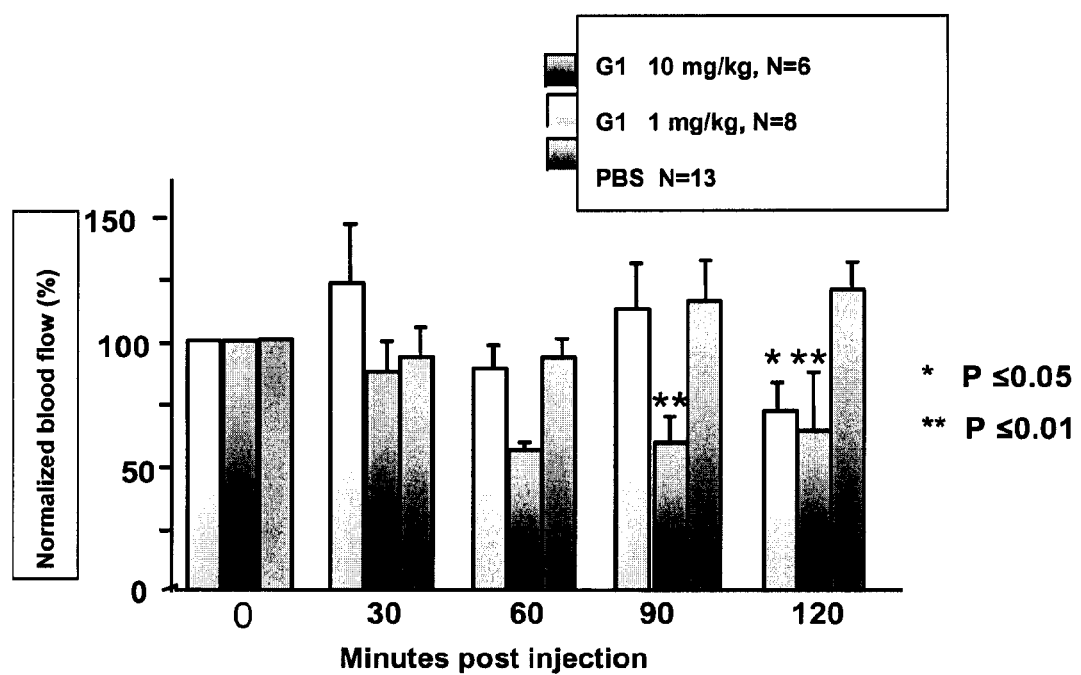
FIG. 9: Data showing G1 inhibits neurogenic flare in the skin starting from 90 min post-treatment. G1 was administered by intravenous administration (1 ml/kg). Data are from 6-8 or 13 rats per group. *p=0.05, **p=0.01 vs vehicle (phosphate buffered saline) treated group at each time point (AVOVA).

Results (FIG. 9) demonstrated that in vehicle treated animals no significant change in blood flow response was but rats treated with G1 showed a significant decrease in blood flow response starting at 90 and 120 minutes post dose for 10 mg/kg and 1mg/kg, respectively. Similar activity was achieved using D2. Additionally in further neurogenic flare and vasodilatation model tests G1 showed marked effect at 7 days post IV dosing (predicted $ED_{50}$=6 ug/ml in saphenous nerve stimulation model). The conclusions form the tests done is that G1 and G2 demonstrate anti-CGRP antagonist activity. Similar CGRP function-blocking ability for the antibodies is also shown in the publication, Zeller J, et. al. Br J Pharmacol. 2008 December; 155(7):1093-103. Epub 2008 Sep. 8.

The following materials have been deposited with the American Type Culture Collection, 10801 University Boulevard, Manassas, Va. 20110-2209, USA (ATCC):

| Material | Antibody No. | ATCC Accession No. | Date of Deposit |
| --- | --- | --- | --- |
| pEb.CGRP.hKGI | G1 heavy chain | PTA-6867 | Jul. 15, 2005 |
| pDb.CGRP.hFcGI | G1 light chain | PTA-6866 | Jul. 15, 2005 |

Vector pEb.CGRP.hKGI is a polynucleotide encoding the G1 light chain variable region and the light chain kappa constant region; and vector pDb.CGRP.hFcGI is a polynucleotide encoding the G1 heavy chain variable region and the heavy chain IgG2 constant region containing the following mutations: A330P331 to S330S331 (amino acid numbering with reference to the wildtype IgG2 sequences; see Eur. J. Immunol. (1999) 29:2613-2624).

Below are given antibody sequences useful for practising the present invention.

Antibody Sequences

Antibody G1 heavy chain variable region amino acid sequence
(SEQ ID NO: 1)
EVQLVESGGGLVQPGGSLRLSCAASGFTFSNYWISWVRQAPGKGLEWV
AEIRSESDASATHYAEAVKGRFTISRDNAKNSLYLQMNSLRAEDTAVY
YCLAYFDYGLAIQNYWGQGTLVTVSS Antibody G1 light chain variable region amino acid sequence
(SEQ ID NO: 2)
EIVLTQSPATLSLSPGERATLSCKASKRVTTYVSWYQQKPGQAPRLLI
YGASNRYLGIPARFSGSGSGTDFTLTISSLEPEDFAVYYCSQSYNYPY
TFGQGTKLEIK Antibody G1 CDR H1 (extended CDR)
(SEQ ID NO: 3)
GFTFSNYWIS Antibody G1 CDR H2 (extended CDR)
(SEQ ID NO: 4)
EIRSESDASATHYAEAVKG Antibody G1 CDR H3
(SEQ ID NO: 5)
YFDYGLAIQNY Antibody G1 CDR L1
(SEQ ID NO: 6)
KASKRVTTYVS Antibody G1 CDR L2
(SEQ ID NO: 7)
GASNRYL Antibody G1 CDR L3
(SEQ ID NO: 8)
SQSYNYPYT Antibody G1 heavy chain variable region nucleotide sequence
(SEQ ID NO: 9)
GAAGTTCAGCTGGTTGAATCCGGTGGTGGTCTGGTTCAGCCAGGTGGT
TCCCTGCGTCTGTCCTGCGCTGCTTCCGGTTTCACCTTCTCCAACTAC
TGGATCTCCTGGGTTCGTCAGGCTCCTGGTAAAGGTCTGGAATGGGTT
GCTGAAATCCGTTCCGAATCCGACGCGTCCGCTACCCATTACGCTGAA
GCTGTTAAAGGTCGTTTCACCATCTCCCGTGACAACGCTAAGAACTCC
CTGTACCTGCAGATGAACTCCCTGCGTGCTGAAGACACCGCTGTTTAC
TACTGCCTGGCTTACTTTGACTACGGTCTGGCTATCCAGAACTACTGG
GGTCAGGGTACCCTGGTTACCGTTTCCTCC Antibody G1 light chain variable region nucleotide sequence
(SEQ ID NO: 10)
GAAATCGTTCTGACCCAGTCCCCGGCTACCCTGTCCCTGTCCCCAGG
TGAACGTGCTACCCTGTCCTGCAAAGCTTCCAAACGGGTTACCACCT
ACGTTTCCTGGTACCAGCAGAAACCCGGTCAGGCTCCTCGTCTGCTG
ATCTACGGTGCTTCCAACCGTTACCTGGTATCCCAGCTCGTTTCTC
CGGTTCCGGTTCCGGTACCGACTTCACCCTGACCATCTCCTCCCTGG
AACCCGAAGACTTCGCTGTTTACTACTGCAGTCAGTCCTACAACTAC
CCCTACACCTTCGGTCAGGGTACCAAACTGGAAATCAAA Antibody G1 heavy chain full antibody amino acid sequence (including modified IgG2 as described herein)
(SEQ ID NO: 11)
EVQLVESGGGLVQPGGSLRLSCAASGFTFSNYWISWVRQAPGKGLEW
VAEIRSESDASATHYAEAVKGRFTISRDNAKNSLYLQMNSLRAEDTA
VYYCLAYFDYGLAIQNYWGQGTLVTVSSASTKGPSVFPLAPCSRSTS
ESTAALGCLVKDYFPEPVTVSWNSGALTSGVHTFPAVLQSSGLYSLS
SVVTVPSSNFGTQTYTCNVDHKPSNTKVDKTVERKCCVECPPCPAPP
VAGPSVFLFPPKPKDTLMISRTPEVTCVVVDVSHEDPEVQFNWYVDG
VEVHNAKTKPREEQFNSTFRVVSVLTVVHQDWLNGKEYKCKVSNKGL
PSSIEKTISKTKGQPREPQVYTLPPSREEMTKNQVSLTCLVKGFYPS
DIAVEWESNGQPENNYKTTPPMLDSDGSFFLYSKLTVDKSRWQQGNV
FSCSVMHEALHNHYTQKSLSLSPGK Antibody G1 light chain full antibody amino acid sequence
(SEQ ID NO: 12)
EIVLTQSPATLSLSPGERATLSCKASKRVTTYVSWYQQKPGQAPRLL
IYGASNRYLGIPARFSGSGSGTDFTLTISSLEPEDFAVYYCSQSYNY
PYTFGQGTKLEIKRTVAAPSVFIFPPSDEQLKSGTASVVCLLNNFYP
REAKVQWKVDNALQSGNSQESVTEQDSKDSTYSLSSTLTLSKADYEK
HKVYACEVTHQGLSSPVTKSFNRGEC Antibody G1 heavy chain full antibody nucleotide sequence (including modified IgG2 as described herein)
(SEQ ID NO: 13)
GAAGTTCAGCTGGTTGAATCCGGTGGTGGTCTGGTTCAGCCAGGTGGT
TCCCTGCGTCTGTCCTGCGCTGCTTCCGGTTTCACCTTCTCCAACTAC
TGGATCTCCTGGGTTCGTCAGGCTCCTGGTAAAGGTCTGGAATGGGTT
GCTGAAATCCGTTCCGAATCCGACGCGTCCGCTACCCATTACGCTGAA
GCTGTTAAAGGTCGTTTCACCATCTCCCGTGACAACGCTAAGAACTCC
CTGTACCTGCAGATGAACTCCCTGCGTGCTGAAGACACCGCTGTTTAC
TACTGCCTGGCTTACTTTGACTACGGTCTGGCTATCCAGAACTACTGG
GGTCAGGGTACCCTGGTTACCGTTTCCTCCGCCTCCACCAAGGGCCCA
TCTGTCTTCCCACTGGCCCCATGCTCCCGCAGCACCTCCGAGAGCACA
GCCGCCCTGGGCTGCCTGGTCAAGGACTACTTCCCAGAACCTGTGACC
GTGTCCTGGAACTCTGGCGCTCTGACCAGCGGCGTGCACACCTTCCCA
GCTGTCCTGCAGTCCTCAGGTCTCTACTCCCTCAGCAGCGTGGTGACC
GTGCCATCCAGCAACTTCGGCACCCAGACCTACACCTGCAACGTAGAT
CACAAGCCAAGCAACACCAAGGTCGACAAGACCGTGGAGAGAAAGTGT
TGTGTGGAGTGTCCACCTTGTCCAGCCCCTCCAGTGGCCGGACCATCC
GTGTTCCTGTTCCCTCCAAAGCCAAAGGACACCCTGATGATCTCCAGA
ACCCCAGAGGTGACCTGTGTGGTGGTGGACGTGTCCCACGAGGACCCA
GAGGTGCAGTTCAACTGGTATGTGGACGGAGTGGAGGTGCACAACGCC
AAGACCAAGCCAAGAGAGGAGCAGTTCAACTCCACCTTCAGAGTGGTG
AGCGTGCTGACCGTGGTGCACCAGGACTGGCTGAACGGAAAGGAGTAT
AAGTGTAAGGTGTCCAACAAGGGACTGCCATCCAGCATCGAGAAGACC
ATCTCAAGACCAAGGGACAGCCAAGAGAGCCACAGGTGTATACCCTG
CCCCCATCCAGAGAGGAGATGACCAAGAACCAGGTGTCCCTGACCTGT
CTGGTGAAGGGATTCTATCCATCCGACATCGCCGTGGAGTGGGAGTCC
AACGGACAGCCAGAGAACAACTATAAGACCACCCCTCCAATGCTGGAC
TCCGACGGATCCTTCTTCCTGTATTCCAAGCTGACCGTGGACAAGTCC
AGATGGCAGCAGGGAAACGTGTTCTCTTGTTCCGTGATGCACGAGGCC
CTGCACAACCACTATACCCAGAAGAGCCTGTCCCTGTCTCCAGGAAAG
TAA Antibody G1 light chain full antibody nucleotide sequence
(SEQ ID NO: 14)
GAAATCGTTCTGACCCAGTCCCCGGCTACCCTGTCCCTGTCCCCAGGT
GAACGTGCTACCCTGTCCTGCAAAGCTTCCAAACGGGTTACCACCTAC
GTTTCCTGGTACCAGCAGAAACCCGGTCAGGCTCCTCGTCTGCTGATC
TACGGTGCTTCCAACCGTTACCTGGTATCCCAGCTCGTTTCTCCGGT
TCCGGTTCCGGTACCGACTTCACCCTGACCATCTCCTCCCTGGAACCC
GAAGACTTCGCTGTTTACTACTGCAGTCAGTCCTACAACTACCCCTAC
ACCTTCGGTCAGGGTACCAAACTGGAAATCAAACGCACTGTGGCTGCA
CCATCTGTCTTCATCTTCCCTCCATCTGATGAGCAGTTGAAATCCGGA
ACTGCCTCTGTTGTGTGCCTGCTGAATAACTTCTATCCGCGCGAGCC
AAAGTACAGTGGAAGGTGGATAACGCCCTCCAATCGGTAACTCCCAG
GAGAGTGTCACAGAGCAGGACAGCAAGGACAGCACCTACAGCCTCAGC
AGCACCCTGACCCTGAGCAAAGCAGACTACGAGAAACACAAAGTCTAC
GCCTGCGAAGTCACCCATCAGGGCCTGAGTTCTCCAGTCACAAAGAGC
TTCAACCGCGGTGAGTGCTAA Amino acid sequence comparison of human and rat CGRP (human α-CGRP (SEQ ID NO: 15); human β-CGRP (SEQ ID NO: 16); rat α-CGRP (SEQ ID NO: 17); and rat β-CGRP (SEQ ID NO: 18)):

(SEQ ID NO: 15)
NH$_2$-ACDTATCVTHRLAGLLSRSGGVVKNNFVPTNVGSKAF-CONH$_2$ (SEQ ID NO: 16)
NH$_2$-ACNTATCVTHRLAGLLSRSGGMVKSNFVPTNVGSKAF-CONH$_2$ (SEQ ID NO: 17)
NH$_2$-SCNTATCVTHRLAGLLSRSGGVVKDNFVPTNVGSEAF-CONH$_2$

```
                                                          (SEQ ID NO: 18)
NH2-[?]C[?]TATCVTHRLAGLLSRSGGVVK[?]NFVPTNVGSKAF-
CONH2

Antibody G2 heavy chain variable region amino
acid sequence
                                                          (SEQ ID NO: 19)
EVQLQQSGPELVKPGASVKMSCKASGYTFTSSVMHWVKQKPGQGL
EWIGYINPYNDGTKYNEKFKGKATLTSDKSSSTAYMELSSLTSED
SAVYYCAKGGNDGYWGQGTTLTVSS Antibody G2 light chain variable region amino
acid sequence
                                                          (SEQ ID NO: 20)
EIVLTQSPTTMAASPGEKITITCSASSSISSIYLHWYQQKPGFSPK
VLIYRASNLASGVPARFSGSGSGTSYSLTIGTMEAEDVATYYCQQG
STIPFTFGSGTKLEIK Antibody G2 CDR H1 (extended CDR)
                                                          (SEQ ID NO: 21)
SSVMH Antibody G2 CDR H2 (extended CDR)
                                                          (SEQ ID NO: 22)
YINPYNDGTKYNEKFKG Antibody G2 CDR H3
                                                          (SEQ ID NO: 23)
GGNDGY Antibody G2 CDR L1
                                                          (SEQ ID NO: 24)
SASSSISSIYLH Antibody G2 CDR L2
                                                          (SEQ ID NO: 25)
RASNLAS Antibody G2 CDR L3
                                                          (SEQ ID NO: 26)
QQGSTIPFT Antibody G2 heavy chain variable region
nucleotide sequence
                                                          (SEQ ID NO: 27)
GAGGTCCAGCTGCAGCAGTCTGGACCTGAGCTGGTAAAGCCTGGGGC
TTCAGTGAAGATGTCCTGCAAGGCTTCTGGATACACATTCACTAGCT
CTGTTATGCACTGGGTGAAGCAGAAGCCTGGGCAGGGCCTTGAGTGG
ATTGGATATATTAATCCTTACAATGATGGTACTAAGTACAATGAGAA
GTTCAAAGGCAAGGCCACACTGACTTCAGACAAATCCTCCAGCACAG
CCTACATGGAACTCAGCAGCCTGACCTCTGAGGACTCTGCGGTCTAT
TACTGTGCAAAAGGGGGTAACGATGGCTACTGGGGCCAAGGCACTAC
TCTCACAGTCTCCTCA Antibody G2 light chain variable region
nucleotide sequence
                                                          (SEQ ID NO: 28)
GAAATTGTGCTCACCCAGTCTCCAACCACCATGGCTGCATCTCCCGG
GGAGAAGATCACTATCACCTGTAGTGCCAGCTCAAGTATAAGTTCCA
TTTACTTGCATTGGTATCAGCAGAAGCCAGGATTCTCCCCTAAAGTC
TTGATTTATAGGGCATCCAATCTGGCTTCTGGAGTCCCAGCTCGCTT
CAGTGGCAGTGGGTCTGGGACCTCTTACTCTCTCACAATTGGCACCA
TGGAGGCTGAAGATGTTGCCACTTACTACTGCCAGCAGGGTAGTACT
ATACCATTCACGTTCGGCTCGGGGACAAAGTTGGAAATAAAA Antibody G2 heavy chain full antibody amino acid
sequence (not including Fc domain)
                                                          (SEQ ID NO: 29)
EVQLQQSGPELVKPGASVKMSCKASGYTFTSSVMHWVKQKPGQGLEW
IGYINPYNDGTKYNEKFKGKATLTSDKSSSTAYMELSSLTSEDSAVY
YCAKGGNDGYWGQGTTLTVSSAKTTPPSVYPLAPGSAAQTNSMVTLG
CLVKGYFPEPVTVTWNSGSLSSGVHTFPAVLQSDLYTLSSSVTVPSS
TWPSETVTCNVAHPASSTKVDKKIVPRD Antibody G2 light chain full antibody amino acid
sequence
                                                          (SEQ ID NO: 30)
EIVLTQSPTTMAASPGEKITITCSASSSISSIYLHWYQQKPGFSPKV
LIYRASNLASGVPARFSGSGSGTSYSLTIGTMEAEDVATYYCQQGST
IPFTFGSGTKLEIKRADAAPTVSIFPPSSEQLTSGGASVVCFLNNFY
PRDINVKWKIDGSERQNGVLNSWTDQDSKDSTYSMSSTLTLTKDEYE
RHNSYTCEATHKTSTSPIVKSFNRNEC Antibody G2 heavy chain full antibody nucleotide
sequence (not including Fc domain)
                                                          (SEQ ID NO: 31)
GAGGTCCAGCTGCAGCAGTCTGGACCTGAGCTGGTAAAGCCTGGGGC
TTCAGTGAAGATGTCCTGCAAGGCTTCTGGATACACATTCACTAGCT
CTGTTATGCACTGGGTGAAGCAGAAGCCTGGGCAGGGCCTTGAGTGG
ATTGGATATATTAATCCTTACAATGATGGTACTAAGTACAATGAGAA
GTTCAAAGGCAAGGCCACACTGACTTCAGACAAATCCTCCAGCACAG
CCTACATGGAACTCAGCAGCCTGACCTCTGAGGACTCTGCGGTCTAT
TACTGTGCAAAAGGGGGTAACGATGGCTACTGGGGCCAAGGCACTAC
TCTCACAGTCTCCTCAGCCAAAACGACACCCCCATCTGTCTATCCAC
TGGCCCCTGGATCTGCTGCCCAAACTAACTCCATGGTGACCCTGGGA
TGCCTGGTCAAGGGCTATTTCCCTGAGCCAGTGACAGTGACCTGGAA
CTCTGGATCCCTGTCCAGCGGTGTGCACACCTTCCCAGCTGTCCTGC
AGTCTGACCTCTACACTCTGAGCAGCTCAGTGACTGTCCCCTCCAGC
ACCTGGCCCAGCGAGACCGTCACCTGCAACGTTGCCCACCCGGCCAG
CAGCACCAAGGTGGACAAGAAAATTGTGCCCAGGGAT Antibody G2 light chain full antibody nucleotide
sequence
                                                          (SEQ ID NO: 32)
GAAATTGTGCTCACCCAGTCTCCAACCACCATGGCTGCATCTCCCGG
GGAGAAGATCACTATCACCTGTAGTGCCAGCTCAAGTATAAGTTCCA
TTTACTTGCATTGGTATCAGCAGAAGCCAGGATTCTCCCCTAAAGTC
TTGATTTATAGGGCATCCAATCTGGCTTCTGGAGTCCCAGCTCGCTT
CAGTGGCAGTGGGTCTGGGACCTCTTACTCTCTCACAATTGGCACCA
TGGAGGCTGAAGATGTTGCCACTTACTACTGCCAGCAGGGTAGTACT
ATACCATTCACGTTCGGCTCGGGGACAAAGTTGGAAATAAAACGGGC
TGATGCTGCACCAACTGTATCCATCTTCCCACCATCCAGTGAGCAGT
TAACATCTGGAGGTGCCTCAGTCGTGTGCTTCTTGAACAACTTCTAC
CCCAGAGACATCAATGTCAAGTGGAAGATTGATGGCAGTGAACGACA
AAATGGTGTCCTGAACAGTTGGACTGATCAGGACAGCAAAGACAGCA
CCTACAGCATGAGCAGCACCCTCACATTGACCAAGGACGAGTATGAA
CGACATAACAGCTATACCTGTGAGGCCACTCACAAGACATCAACTTC
ACCCATCGTCAAGAGCTTCAACAGGAATGAGTGTTAA
```

The invention claimed is:

1. A method of treatment of chronic bone cancer pain and/or symptoms of chronic bone cancer pain in an individual, the method comprising administering to the individual a therapeutically effective amount of an anti-CGRP antagonist antibody.

2. The method according to claim 1, wherein the anti-CGRP antagonist antibody is peripherally administered.

3. The method according to claim 1, wherein the anti-CGRP antagonist antibody is administered orally, sublingually, via inhalation, transdermally, subcutaneously, intravenously, intra-arterially, intra-articularly, peri-articularly, locally and/or intramuscularly.

4. The method according to claim 3, wherein the anti-CGRP antagonist antibody is administered subcutaneously or intravenously.

5. The method according to claim 1, wherein the anti-CGRP antagonist antibody acts peripherally on administration.

6. The method according to claim 1, wherein the chronic bone cancer pain further comprises one or more of hyperalgesia, allodynia, central sensitisation, peripheral sensitisation, disinhibition and augmented facilitation.

7. The method according to claim 1, wherein the chronic bone cancer pain is pain due to one or more of the following conditions: myeloma in bone marrow, sarcoma in connective or supportive tissue, cancer of bone tissue, cancer of blood-forming cells, cancer of bone marrow, multiple myeloma, leukaemia, primary or secondary bone cancer, tumours that metastasize to the bone, bone tumours infiltrating the nerve and hollow viscus, and bone tumours near neural structures.

8. The method according to claim 1, wherein the anti-CGRP antagonist antibody: (a) binds to CGRP; (b) blocks CGRP from binding to its receptor; (c) blocks or decreases CGRP receptor activation; (d) inhibits blocks, suppresses or reduces CGRP biological activity; (e) increases clearance of CGRP; and/or (g) inhibits CGRP synthesis, production or release.

9. The method according to claim 1, wherein the anti-CGRP antagonist antibody: (i) is a human antibody, (ii) is a humanized antibody, (iii) is a monoclonal antibody, (iv) binds CGRP with a Kd of 50 nM or less (as measured by surface plasmon resonance at 37° C.); and/or (v) has a half life in-vivo of at least 7 days.

10. The method according to claim 9, wherein the anti-CGRP antagonist antibody specifically binds to amino acid residues 33-37 of SEQ ID NO:15.

11. The method according to claim 1, wherein the anti-CGRP antagonist antibody specifically binds to the C-terminal region of CGRP.

12. The method according to claim 1, wherein the anti-CGRP antibody comprises:
(a) CDR H1 as set forth in SEQ ID NO: 3 or 21;
(b) CDR H2 as set forth in SEQ ID NO: 4 or SEQ ID NO: 22;
(c) CDR H3 as set forth in SEQ ID NO: 5 or 23;
(d) CDR L1 as set forth in SEQ ID NO: 6 or SEQ ID NO: 24;
(e) CDR L2 as set forth in SEQ ID NO: 7 or SEQ ID NO: 25;
(f) CDR L3 as set forth in SEQ ID NO: 8 or 26;
wherein the antibody binds CGRP with a Kd of 50 nM or less as measured by surface plasmon resonance at 37° C.

13. The method according to claim 1, wherein the anti-CGRP antibody comprises a VH domain that comprises the amino acid sequence to SEQ ID NO: 1 and a VL domain that comprises the amino acid sequence to SEQ ID NO: 2.

14. The method according to claim 1, wherein the anti-CGRP antibody comprises a) a heavy chain produced by the expression vector with ATCC Accession No. PTA-6867; b) a light chain produced by the expression vector with ATCC Accession No. PTA-6866 or c) an anti-CGRP antibody produced by the expression vectors with ATCC Accession Nos. PTA-6867 and PTA-6866.

* * * * *